United States Patent
Haruta

(10) Patent No.: US 12,343,472 B2
(45) Date of Patent: Jul. 1, 2025

(54) POWDER PREPARATION, CARTRIDGE, AND DEVICE

(71) Applicant: Shin Nippon Biomedical Laboratories, Ltd., Kagoshima (JP)

(72) Inventor: Shunji Haruta, Kagoshima (JP)

(73) Assignee: Shin Nippon Biomedical Laboratories, Ltd., Kagoshima (JP)

( * ) Notice: Subject to any disclaimer, the term of this patent is extended or adjusted under 35 U.S.C. 154(b) by 948 days.

(21) Appl. No.: 16/975,701

(22) PCT Filed: Feb. 7, 2019

(86) PCT No.: PCT/JP2019/004331
§ 371 (c)(1),
(2) Date: Aug. 25, 2020

(87) PCT Pub. No.: WO2019/163520
PCT Pub. Date: Aug. 29, 2019

(65) Prior Publication Data
US 2020/0405983 A1    Dec. 31, 2020

(30) Foreign Application Priority Data
Feb. 26, 2018   (JP) .................. 2018-032498

(51) Int. Cl.
*A61M 15/08*      (2006.01)
*A61K 9/00*       (2006.01)
(Continued)

(52) U.S. Cl.
CPC ........... *A61M 15/08* (2013.01); *A61K 9/0075* (2013.01); *A61K 9/14* (2013.01); *A61K 45/06* (2013.01);
(Continued)

(58) Field of Classification Search
None
See application file for complete search history.

(56) References Cited

U.S. PATENT DOCUMENTS 6,465,626 B1    10/2002  Watts et al.
8,827,946 B2 *   9/2014  Tsutsui ............... A61M 15/004
                                                    604/514
(Continued)

FOREIGN PATENT DOCUMENTS

EP     2 116 264 A1    11/2009
EP     2 403 490 A      1/2012
(Continued)

OTHER PUBLICATIONS

Princy Agarwal, Anju Goyal and Rajat Vaishnav Comparative Quality Assessment of Three Different Marketed Brands of Indian Polyherbal Formulation—Triphala Churna http://dx.doi.org/10.26717/BJSTR.2018.05.001237 (Year: 2018).*
(Continued)

*Primary Examiner* — Robert A Wax
*Assistant Examiner* — Andre Mach
(74) *Attorney, Agent, or Firm* — Finnegan, Henderson, Farabow, Garrett & Dunner, LLP

(57) ABSTRACT

An object of the present invention is to provide a powder preparation and the like suitable for selective administration to an olfactory region and the like. The object is achieved by a powder preparation for selectively administering an active ingredient to an olfactory region in a nasal cavity, the powder preparation comprising the active ingredient and having a bulk density of 0.1 to 0.5 g/cm$^3$ and a Hausner ratio of 1.6 to 2.4.

16 Claims, 9 Drawing Sheets

(51) Int. Cl.
  *A61K 9/14* (2006.01)
  *A61K 45/06* (2006.01)
  *A61M 11/00* (2006.01)
  *A61M 15/00* (2006.01)

(52) U.S. Cl.
  CPC ...... *A61M 11/001* (2014.02); *A61M 15/0065* (2013.01); *A61M 15/0086* (2013.01); *A61M 2202/064* (2013.01)

(56) References Cited

U.S. PATENT DOCUMENTS

| | | | |
|---|---|---|---|
| 2002/0158150 A1 | 10/2002 | Matsugi et al. | |
| 2009/0308390 A1* | 12/2009 | Smutney | A61K 38/28 128/203.15 |
| 2010/0178331 A1 | 7/2010 | Nagata et al. | |
| 2010/0288276 A1 | 11/2010 | Ganderton et al. | |
| 2013/0095145 A1* | 4/2013 | Nagata | A61P 11/00 424/400 |
| 2013/0213398 A1 | 8/2013 | Lipp et al. | |
| 2013/0266653 A1 | 10/2013 | Lipp et al. | |
| 2014/0014106 A1 | 1/2014 | Smutney et al. | |
| 2015/0136130 A1 | 5/2015 | DeHaan et al. | |
| 2015/0144129 A1* | 5/2015 | Djupesland | A61M 15/08 128/203.18 |
| 2016/0101245 A1 | 4/2016 | Hoekman et al. | |
| 2017/0128364 A1 | 5/2017 | Kamishita et al. | |

FOREIGN PATENT DOCUMENTS

| | | | |
|---|---|---|---|
| JP | 2001-131057 A | 5/2001 | |
| JP | 2002-255795 A | 9/2002 | |
| JP | 2013-536845 A | 9/2013 | |
| JP | 2014-028848 A | 2/2014 | |
| JP | 2015-509788 A | 4/2015 | |
| JP | 2016-135272 | 7/2016 | |
| JP | 2016-520378 A | 7/2016 | |
| KR | 2010-0091970 A | 8/2010 | |
| KR | 2013-0098370 A | 9/2013 | |
| WO | WO-2001/095962 | 12/2001 | |
| WO | WO 2010/102148 A2 | 9/2010 | |
| WO | WO-2012030647 A1 * | 3/2012 | A61K 31/137 |
| WO | WO 2012/044736 A1 | 4/2012 | |
| WO | WO-2014165303 A1 * | 10/2014 | A61K 31/439 |
| WO | WO-2015/199130 | 12/2015 | |
| WO | WO2016/196401 A | 12/2016 | |

OTHER PUBLICATIONS

International Search Report from the Japanese Patent Office for International Application No. PCT/JP2019/004331 mailed Apr. 23, 2019.

* cited by examiner

POWDER PREPARATION, CARTRIDGE, AND DEVICE

This application is a national stage filing under 35 U.S.C. § 371 of International Application No. PCT/JP2019/004331, filed on Feb. 7, 2019, and published as WO/2019/163520, which claims priority to Japanese Patent Application No. 2018-032498, filed on Feb. 26, 2018. International Application No. PCT/JP2019/004331 is incorporated herein by reference in its entirety.

TECHNICAL FIELD

The present application claims priority to Japanese Patent Application No. 2018-32498 (filed on Feb. 26, 2018). The entire contents of the Japanese Patent Application are incorporated herein by reference.

The present invention relates to a powder preparation for selectively administering an active ingredient to a specific region in the nasal cavity. The present invention also relates to a cartridge containing the powder preparation. Moreover, the invention relates to a device containing the cartridge.

BACKGROUND ART

Conventionally, intranasal administration has been primarily intended for local treatment such as rhinitis treatment. However, recently, attempts are being made to use intranasal administration to prevent or treat systemic diseases, central nervous system diseases, infections, and the like, and various intranasal administration preparations and intranasal administration apparatuses have been reported.

For example, Patent Literature 1 discloses "a powdery composition for intranasal administration, which is prepared by mixing a drug and a base using a mixer providing shearing force and which unlikely forms clumps" as a powdery composition for intranasal administration capable of being precisely filled into an intranasal dosing apparatus for multiple administrations and capable of being precisely and uniformly sprayed after being filled.

Patent Literature 2 discloses a powdered medicine multi-dose administrating device having a predetermined structure, as a device which satisfies the requirements of spaying the medicine in a predetermined amount, having a small size (portability), an easy and quick operation, an easy production step, a dispersion of the powdered medicine and a decreased number of parts, low cost, and the like.

Moreover, Patent Literature 3 discloses a nasal spray nozzle for administering a viscous preparation to the nasal mucosa.

The entire contents of the documents cited herein are incorporated herein by reference.

CITATION LIST

Patent Literature

Patent Literature 1: Japanese Patent Laid-Open No. 2002-255795
Patent Literature 2: International Publication No. WO 01/95962
Patent Literature 3: International Publication No. WO 2015-199130.

SUMMARY OF INVENTION

Technical Problem

In order to effectively prevent and/or treat various diseases by intranasal administration, it is necessary to selectively administer an active ingredient to a specific region in the nasal cavity according to the type of the target disease.

Specifically, in order to prevent and/or treat central nervous system diseases, or to perform an examination or diagnosis or a pre-operational or pre-examination treatment based on action on the central nervous system, the active ingredient needs to be selectively administered to the olfactory region in the nasal cavity. The active ingredient administered to the olfactory region can directly migrate to the brain without passing through the blood-brain barrier.

In order to prevent and/or treat systemic diseases, or perform an examination or diagnosis or a pre-operational or pre-examination treatment, it is necessary to selectively administer an active ingredient to the respiratory region in the nasal cavity. For example, the respiratory region has a reticulately developed vascular system and thus superior absorption of an active ingredient and, also, the hepatic first-pass effect can be avoided by passing through the respiratory region, thus enabling the active ingredient to efficiently circulate the entire body. The respiratory region has nasopharynx-related lymphoid tissue important for antigen uptake, and thus infections can also be effectively prevented and/or treated by selectively administering a vaccine as an active ingredient to the respiratory region.

An object of the present invention is to provide a powder preparation suitable for selective administration to the olfactory region or the respiratory region, a cartridge containing the powder preparation, and a device containing the cartridge.

Solution to Problem

The present inventors found that, according to the target region in the nasal cavity, a powder preparation can be selectively administered to the region by changing the predetermined physical properties of the powder preparation, and accomplished the present invention. Specifically, the present invention includes the following embodiments.

[1]
A powder preparation for selectively administering an active ingredient to an olfactory region in a nasal cavity, the powder preparation comprising the active ingredient and having:
a bulk density of 0.1 to 0.5 g/cm³, and
a Hausner ratio of 1.6 to 2.4.
[1-A1]
The powder preparation according to [1], wherein the bulk density is 0.1 to 0.4 g/cm³.
[1-A2]
The powder preparation according to [1], wherein the bulk density is 0.2 to 0.4 g/cm³.
[1-A3]
The powder preparation according to [1], wherein the bulk density is 0.2 to 0.35 g/cm³.
[1-A4]
The powder preparation according to [1], wherein the bulk density is 0.2 to 0.3 g/cm³.
[1-B1]
The powder preparation according to any one of [1] to [1-A4], wherein the Hausner ratio is 1.6 to 2.3.
[1-B2]
The powder preparation according to any one of [1] to [1-A4], wherein the Hausner ratio is 1.6 to 2.2.
[1-B3]
The powder preparation according to any one of [1] to [1-A4], wherein the Hausner ratio is 1.7 to 2.2.

[1-B4]
The powder preparation according to any one of [1] to [1-A4], wherein the Hausner ratio is 1.8 to 2.2.

[1-C1]
The powder preparation according to any one of [1] to [1-B4], having a tap density of 0.1 to 0.8 g/cm$^3$.

[1-C2]
The powder preparation according to any one of [1] to [1-B4], having a tap density of 0.1 to 0.6 g/cm$^3$.

[1-C3]
The powder preparation according to any one of [1] to [1-B4], having a tap density of 0.2 to 0.6 g/cm$^3$.

[1-C4]
The powder preparation according to any one of [1] to [1-B4], having a tap density of 0.3 to 0.55 g/cm$^3$.

[2]
The powder preparation according to any one of [1] to [1-C4], having a specific surface area of 0.3 to 2.5 m$^2$/g.

[2-1]
The powder preparation according to [2], wherein the specific surface area is 0.4 to 2.4 m$^2$/g.

[2-2]
The powder preparation according to [2], wherein the specific surface area is 0.6 to 2.3 m$^2$/g.

[2-3]
The powder preparation according to [2], wherein the specific surface area is 0.8 to 2.3 m$^2$/g.

[3]
The powder preparation according to any one of [1] to [2-3], having an average particle diameter of 10 to 150 μm.

[3-1]
The powder preparation according to [3], wherein the average particle diameter is 10 to 120 μm.

[3-2]
The powder preparation according to [3], wherein the average particle diameter is 10 to 80 μm.

[3-3]
The powder preparation according to [3], wherein the average particle diameter is 10 to 60 μm.

[4]
The powder preparation according to any one of [1] to [3-3], wherein a maximum air pressure for delivering the powder preparation into a nasal cavity is 15 to 100 kPa.

[4-1]
The powder preparation according to [4], wherein the maximum air pressure is 15 to 80 kPa.

[4-2]
The powder preparation according to [4], wherein the maximum air pressure is 15 to 60 kPa.

[4-3]
The powder preparation according to [4], wherein the maximum air pressure is 15 to 40 kPa.

[5]
The powder preparation according to any one of [4] to [4-3], wherein a time until reaching a maximum air pressure is 0 to 40 msec.

[5-1]
The powder preparation according to [5], wherein the time until reaching the maximum air pressure is 0 to 30 msec.

[5-2]
The powder preparation according to [5], wherein the time until reaching the maximum air pressure is 0 to 20 msec.

[5-3]
The powder preparation according to [5], wherein the time until reaching the maximum air pressure is 0 to 10 msec.

[6]
The powder preparation according to any one of [1] to [5-3], wherein a time for which the powder preparation is continuously delivered at an air pressure of 10 kPa or more is 15 to 150 msec.

[6-1]
The powder preparation according to [6], wherein the time for which the powder preparation is continuously delivered at an air pressure of 10 kPa or more is 15 to 100 msec.

[6-2]
The powder preparation according to [6], wherein the time for which the powder preparation is continuously delivered at an air pressure of 10 kPa or more is 25 to 100 msec.

[6-3]
The powder preparation according to [6], wherein the time for which the powder preparation is continuously delivered at an air pressure of 10 kPa or more is 25 to 80 msec.

[7]
The powder preparation according to any one of [1] to [6-3], for preventing and/or treating a central nervous system disease, or for performing an examination or diagnosis or a pre-operational or pre-examination treatment based on action on a central nervous system.

[8]
A cartridge comprising the powder preparation according to any one of [1] to [7].

[9]
A device comprising:
the cartridge according to [8], and
a sprayer for delivering the powder preparation contained in the cartridge.

[9-1]
The device according to [9], wherein the sprayer is configured to achieve the maximum air pressure defined in any one of [4] to [4-3].

[9-2]
The device according to [9] or [9-1], wherein the sprayer is configured to achieve the time until reaching the maximum air pressure defined in any one of [5] to [5-3].

[9-3]
The device according to any one of [9] to [9-2], wherein the sprayer is configured to achieve the time, for which the powder preparation is continuously injected at an air pressure of 10 kPa or more, defined in any one of [6] to [6-3].

[10]
A powder preparation for selectively administering an active ingredient to a respiratory region in a nasal cavity, the powder preparation comprising the active ingredient and having:
a bulk density of 0.2 to 1.1 g/cm$^3$, and
a Hausner ratio of 1.0 to 2.2.

[10-A1]
The powder preparation according to [10], wherein the bulk density is 0.2 to 0.8 g/cm$^3$.

[10-A2]
The powder preparation according to [10], wherein the bulk density is 0.2 to 0.7 g/cm$^3$.

[10-A3]
The powder preparation according to [10], wherein the bulk density is 0.2 to 0.6 g/cm$^3$.

[10-A4]
The powder preparation according to [10], wherein the bulk density is 0.2 to 0.5 g/cm$^3$.
[10-A5]
The powder preparation according to [10], wherein the bulk density is 0.25 to 0.4 g/cm$^3$.
[10-B1]
The powder preparation according to any one of [10] to [10-A5], wherein the Hausner ratio is 1.1 to 2.2.
[10-B2]
The powder preparation according to any one of [10] to [10-A5], wherein the Hausner ratio is 1.2 to 2.2.
[10-B3]
The powder preparation according to any one of [10] to [10-A5], wherein the Hausner ratio is 1.3 to 2.2.
[10-B4]
The powder preparation according to any one of [10] to [10-A5], wherein the Hausner ratio is 1.4 to 2.1.
[10-B5]
The powder preparation according to any one of [10] to [10-A5], wherein the Hausner ratio is 1.5 to 2.0.
[10-C1]
The powder preparation according to any one of [10] to [10-B5], having a tap density of 0.2 to 1.0 g/cm$^3$.
[10-C2]
The powder preparation according to any one of [10] to [10-B5], having a tap density of 0.2 to 0.8 g/cm$^3$.
[10-C3]
The powder preparation according to any one of [10] to [10-B5], having a tap density of 0.3 to 0.9 g/cm$^3$.
[10-C4]
The powder preparation according to any one of [10] to [10-B5], having a tap density of 0.4 to 0.7 g/cm$^3$.
[10-C5]
The powder preparation according to any one of [10] to [10-B5], having a tap density of 0.4 to 0.6 g/cm$^3$.
[11]
The powder preparation according to any one of [10] to [10-C5], having a specific surface area of 0.2 to 2.5 m$^2$/g.
[11-1]
The powder preparation according to [11], wherein the specific surface area is 0.2 to 2.4 m$^2$/g.
[11-2]
The powder preparation according to [11], wherein the specific surface area is 0.2 to 2.2 m$^2$/g.
[11-3]
The powder preparation according to [11], wherein the specific surface area is 0.3 to 2.1 m$^2$/g.
[12]
The powder preparation according to any one of [10] to [11-3], having an average particle diameter of 10 to 500 μm.
[12-1]
The powder preparation according to [12], wherein the average particle diameter is 10 to 300 μm.
[12-2]
The powder preparation according to [12], wherein the average particle diameter is 15 to 250 μm.
[12-3]
The powder preparation according to [12], wherein the average particle diameter is 15 to 200 μm.
[12-4]
The powder preparation according to [12], wherein the average particle diameter is 15 to 150 μm.
[13]
The powder preparation according to any one of [10] to [12-4], wherein a maximum air pressure for delivering the powder preparation into a nasal cavity is 5 to 50 kPa.
[13-1]
The powder preparation according to [13], wherein the maximum air pressure is 5 to 40 kPa.
[13-2]
The powder preparation according to [13], wherein the maximum air pressure is 5 to 30 kPa.
[13-3]
The powder preparation according to [13], wherein the maximum air pressure is 5 to 20 kPa.
[14]
The powder preparation according to any one of [13] to [13-3], wherein a time until reaching a maximum air pressure is 0 to 150 msec.
[14-1]
The powder preparation according to [14], wherein the time until reaching the maximum air pressure is 0 to 130 msec.
[14-2]
The powder preparation according to [14], wherein the time until reaching the maximum air pressure is 5 to 120 msec.
[14-3]
The powder preparation according to [14], wherein the time until reaching the maximum air pressure is 10 to 120 msec.
[15]
The powder preparation according to any one of [10] to [14-3], wherein a time for which the powder preparation is continuously delivered at an air pressure of 5 kPa or more is 30 to 200 msec.
[15-1]
The powder preparation according to [15], wherein the time for which the powder preparation is continuously delivered at an air pressure of 5 kPa or more is 30 to 150 msec.
[15-2]
The powder preparation according to [15], wherein the time for which the powder preparation is continuously delivered at an air pressure of 5 kPa or more is 40 to 150 msec.
[15-3]
The powder preparation according to [15], wherein the time for which the powder preparation is continuously delivered at an air pressure of 5 kPa or more is 60 to 150 msec.
[16]
The powder preparation according to any one of [10] to [15-3], for preventing and/or treating a systemic disease, or for performing an examination or diagnosis or a pre-operational or pre-examination treatment.
[17]
The powder preparation according to any one of [10] to [15-3] for preventing and/or treating an infection.
[18]
A cartridge comprising the powder preparation according to any one of [10] to [17].
[19]
A device comprising:
the cartridge according to [18], and
a sprayer for delivering the powder preparation contained in the cartridge.
[19-1]

The device according to [19], wherein the sprayer is configured to achieve the maximum air pressure defined in any one of [13] to [13-3].

[19-2]

The device according to [19] or [19-1], wherein the sprayer is configured to achieve the time until reaching the maximum air pressure defined in any one of [14] to [14-3].

[19-3]

The device according to any one of [19] to [19-2], wherein the sprayer is configured to achieve the time, for which the powder preparation is continuously delivered at an air pressure of 5 kPa or more, defined in any one of [15] to [15-3].

The present invention further includes the following embodiments.

[A1]

A method for selectively administering an active ingredient to an olfactory region in a nasal cavity, the method comprising delivering into the nasal cavity a powder preparation comprising the active ingredient and having a bulk density of 0.1 to 0.5 g/cm$^3$ and a Hausner ratio of 1.6 to 2.4.

[A2]

A method for selectively administering an active ingredient to a respiratory region in a nasal cavity, the method comprising delivering into the nasal cavity a powder preparation comprising the active ingredient and having a bulk density of 0.2 to 1.1 g/cm$^3$ and a Hausner ratio of 1.0 to 2.2.

[B1]

Use of a powder preparation comprising an active ingredient and having a bulk density of 0.1 to 0.5 g/cm$^3$ and a Hausner ratio of 1.6 to 2.4 for selectively administering the active ingredient to an olfactory region in a nasal cavity.

[B2]

Use of a powder preparation comprising an active ingredient and having a bulk density of 0.2 to 1.1 g/cm$^3$ and a Hausner ratio of 1.0 to 2.2 for selectively administering the active ingredient to a respiratory region in a nasal cavity.

Embodiments [A1] and [B1] may further have the features defined in embodiments [1] to [9-3].

Embodiments [A2] and [B2] may further have one or more of the features defined in embodiments [10] to [19-3].

Advantageous Effects of Invention

The present invention is capable of providing a powder preparation suitable for selective administration to the olfactory region or the respiratory region, a cartridge containing the powder preparation, and a device containing the cartridge.

DESCRIPTION OF EMBODIMENTS

Figure 1:
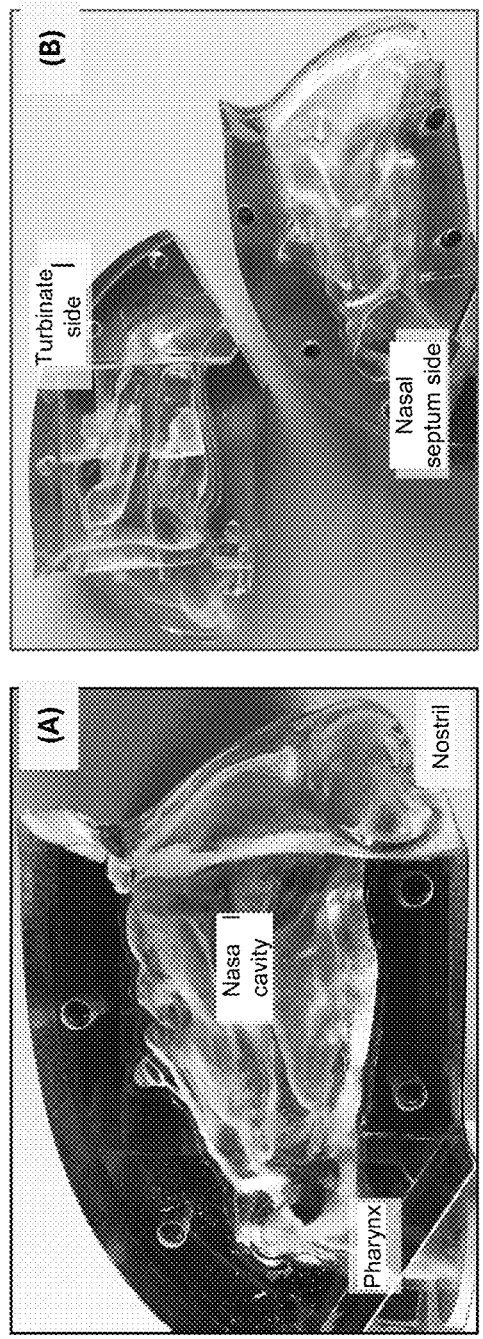
FIG. 1 shows a human nasal cavity model created using a 3D printer.

Below, each of a powder preparation for selectively administering an active ingredient to the olfactory region in the nasal cavity (hereinafter referred to as an "olfactory region powder preparation") and a powder preparation for selectively administering an active ingredient to the respiratory region in the nasal cavity (hereinafter referred to as a "respiratory region powder preparation") will now be described.

<Olfactory Region Powder Preparation>

One embodiment of the present invention relates to a powder preparation for selectively administering an active ingredient to the olfactory region in the nasal cavity, the powder preparation containing the active ingredient and having a bulk density of 0.1 to 0.5 g/cm$^3$ and a Hausner ratio of 1.6 to 2.4.

Selectively administering an active ingredient to the olfactory region in the nasal cavity enables the active ingredient to directly migrate to the brain without passing through the blood-brain barrier. That is to say, selective administration to the olfactory region enables the active ingredient to be efficiently delivered to the brain. As a result, central nervous system diseases can be effectively prevented and/or treated.

The term olfactory region is commonly used in the art (e.g., Der Pharmacia Sinica, 2011, 2(3): 94-106, and Pharm Res (2016) 33: 1527-1541). Herein, specifically, the olfactory region means a region that is within the range from the nasal valve located in the anterior part of the nasal cavity to just before the pharyngeal orifice of the eustachian tube located in the posterior part of the nasal cavity and that consists of a portion covering the superior turbinate located on the canopy of the nasal cavity and a septum-side portion facing it.

Selective administration to the olfactory region means that preferably 20% by weight or more, more preferably 35% by weight or more, further preferably 50% by weight or more, and particularly preferably 60% by weight or more of the active ingredient delivered into the nasal cavity is distributed in the olfactory region. There is no particular upper limit, and the upper limit may be, for example, 90% by weight, 80% by weight, or 70% by weight. The amount of the active ingredient distributed in the olfactory region can be measured according to the method involving a human nasal cavity model described in the following Examples. The proportion of the olfactory region relative to all regions in the nasal cavity is very small, and, therefore, that the above amount of the active ingredient is distributed in the olfactory region means that the concentration of the active ingredient in the olfactory region is significantly higher than the concentrations in other regions.

The bulk density of the olfactory region powder preparation is 0.1 to 0.5 g/cm$^3$, preferably 0.1 to 0.4 g/cm$^3$, more preferably 0.2 to 0.4 g/cm$^3$, further preferably 0.2 to 0.35 g/cm$^3$, and particularly preferably 0.2 to 0.3 g/cm$^3$. The bulk density can be measured according to the method described in the following Examples. The bulk density indicates the specific gravity of the olfactory region powder preparation. When the bulk density is at the above value, the olfactory region selectivity of the active ingredient is improved. The olfactory region powder preparation preferably has a lower bulk density than the respiratory region powder preparation described below.

The Hausner ratio of the olfactory region powder preparation is 1.6 to 2.4, preferably 1.6 to 2.3, more preferably 1.6 to 2.2, further preferably 1.7 to 2.2, and particularly preferably 1.8 to 2.2. The Hausner ratio can be measured according to the method described in the following Examples. The Hausner ratio indicates the flowability of the olfactory region powder preparation. When the Hausner ratio is at the above value, the olfactory region selectivity of the active ingredient is improved.

Conventional nasal powder preparations generally have high flowability. On the other hand, the olfactory region powder preparation according to one embodiment of the present invention has a lower flowability than conventional preparations. Due to the low-flowability characteristics, the olfactory region selectivity of the active ingredient is improved. The olfactory region powder preparation preferably has a lower flowability than the respiratory region powder preparation described below. Poor flowability can also be expressed as having high aggregability or low dispersibility.

According to The Japanese Pharmacopoeia, Seventeenth Edition, the relationship between the Hausner ratio and flowability is described as follows:

Hausner ratio: Degree of flowability
1.00 to 1.11: Very good
1.12 to 1.18: Good
1.19 to 1.25: Slightly good
1.26 to 1.34: Normal
1.35 to 1.45: Slightly poor
1.46 to 1.59: Poor
>1.60: Very poor The tap density of the olfactory region powder preparation is preferably 0.1 to 0.8 g/cm$^3$, more preferably 0.1 to 0.6 g/cm$^3$, further preferably 0.2 to 0.6 g/cm$^3$, and particularly preferably 0.3 to 0.55 g/cm$^3$. The tap density can be measured according to the method described in the following Examples. When the tap density is at the above value, the olfactory region selectivity of the active ingredient is improved.

The specific surface area of the olfactory region powder preparation is preferably 0.3 to 2.5 m$^2$/g, more preferably 0.4 to 2.4 m$^2$/g, further preferably 0.6 to 2.3 m$^2$/g, and particularly preferably 0.8 to 2.3 m$^2$/g. The specific surface area can be measured according to the method described in the following Examples. When the specific surface area is at the above value, the olfactory region selectivity of the active ingredient is improved.

The average particle diameter of the olfactory region powder preparation is preferably 10 to 150 μm, more preferably 10 to 120 μm, further preferably 10 to 80 μm, and particularly preferably 10 to 60 μm. The average particle diameter can be measured according to the method described in the following Examples. When the average particle diameter is at the above value, the olfactory region selectivity of the active ingredient is improved.

The olfactory region powder preparation is preferably delivered into the nasal cavity at a predetermined air pressure. The maximum air pressure for delivering the olfactory region powder preparation into the nasal cavity (hereinafter referred to as the "maximum air pressure") is preferably 15 to 100 kPa, more preferably 15 to 80 kPa, further preferably 15 to 60 kPa, and particularly preferably 15 to 40 kPa. The maximum air pressure can be measured according to the method described in the following Examples. When the maximum air pressure is at the above value, the olfactory region selectivity of the active ingredient is improved.

The time until reaching the maximum air pressure (hereinafter referred to as the "maximum air pressure reaching time") is preferably 0 to 40 msec, more preferably 0 to 30 msec, further preferably 0 to 20 msec, and particularly preferably 0 to 10 msec. The maximum air pressure reaching time can be measured according to the method described in the following Examples. When the maximum air pressure reaching time is at the above value, the olfactory region selectivity of the active ingredient is improved.

The time of continuous delivery at an air pressure of 10 kPa or more (hereinafter referred to as the "constant air pressure continuous delivery time (≥10 kPa)") is preferably 15 to 150 msec, more preferably 15 to 100 msec, further preferably 25 to 100 msec, and particularly preferably 25 to 80 msec. The constant air pressure continuous delivery time (≥10 kPa) can be measured according to the method described in the following Examples. When the constant air pressure continuous delivery time (≥10 kPa) is at the above value, the olfactory region selectivity of the active ingredient is improved.

The olfactory region powder preparation is preferably delivered at a higher air pressure and in a shorter period of time than the respiratory region powder preparation described below.

The administration target of the olfactory region powder preparation is not particularly limited, and is preferably a human. The olfactory region powder preparation is suitable for selectively administering an active ingredient to the olfactory region, especially in the human nasal cavity structure.

The olfactory region powder preparation enables the active ingredient to directly migrate to the brain, and is thus effective for preventing and/or treating central nervous system diseases and the like, or performing an examination or diagnosis or a pre-operative or pre-examination treatment based on action on the central nervous system. Examples of central nervous system diseases include cerebral hemorrhage, cerebral infarction, infections of the central nervous system, brain tumor, Parkinson's disease, epilepsy, amyotrophic lateral sclerosis, Alzheimer's disease, Lewy body dementia, progressive supranuclear palsy, corticobasal degeneration, Pick's disease, frontotemporal dementia, multiple sclerosis, schizophrenia, depression, bipolar disorder, dysthymia, adjustment disorder, social anxiety disorder, panic disorder, obsessive-compulsive disorder, autism spectrum disorder, attention deficit/hyperactivity disorder, sleep disorder, insomnia, traumatic brain injury, pain, and migraine. Examples of the examination or diagnosis or the pre-operational or pre-examination treatment based on action on the central nervous system include imaging, anesthesia, sedation, analgesia, and antianxiety.

Examples of the modality of the active ingredient of the olfactory region powder preparation include, but are not particularly limited to, low molecule compounds, middle molecule drugs including peptide drugs, protein medicaments including antibody medicaments, nucleic acid medicaments, cellular medicaments, regenerative medicine, and vaccine antigens including peptide antigens.

Examples of the active ingredient of the olfactory region powder preparation include, but are not particularly limited to, components effective for preventing and/or treating central nervous system diseases, or for an examination or diagnosis or a pre-operative or pre-examination treatment based on action on the central nervous system, or the like. Examples of the active ingredient include tissue plasminogen activators, edaravone, ozagrel sodium, selective thrombin inhibitors, acyclovir, vidarabine, vancomycin, ceftazidime, ampicillin, panipenem-betamipron, dexamethasone, cisplatin, carboplatin, vincristine, cyclophosphamide, ifosfamide, temozolomide, etoposide, L-dopa, adrenaline, amphetamine, apomorphine, amantadine, cabergoline, zonisamide, droxidopa, piperiden, phenobarbital, phenytoin, primidone, ethosuximide, zonisamide, clonazepam, midazolam, remimazolam, sodium valproate, carbamazepine, gabapentin, topiramate, cannabide, donepezil, rivastigmine, galantamine, memantine, dimethyl fumarate, natalizumab, haloperidol, spiperone, fluphenazine, chlorpromazine, risperidone, blonanserin, quetiapine, olanzapine, aripiprazole, brexpiprazole, triazolam, zopiclone, zolpidem, etizolam, lormetazepam, bromvalerylurea, chloral hydrate, pentobarbital, rilmazaphone, oxytocin, vasopressin, desmopressin, insulin, GLP-1, glucagon, growth hormone, IGF-1, leuprorelin, leptin, guanfasin, methylphenidate, atomoxetine, progesterone, morphine, codeine, oxycodone, fentanyl, hydromorphone, butorphanol, tramadol, buprenorphine, ibuprofen, loxoprofen, sumatriptan, zolmitriptan, dihydroergotamine, rizatriptan, erenumab, galcanezumab, fremanezumab, fomivirsen, mipomersen, nusinersen, cyclosporine, tacrolimus, fluorodeoxyglucose, fluorothymidine, iopamidol, thallium, manganese, and technesium. The active ingredients may be used singly or in combinations of two or more.

The olfactory region powder preparation may contain a base in addition to the active ingredient. Examples of the base include saccharides and amino acids that are applicable to the mucosa of a living body. The bases may be used singly or in combinations of two or more.

Examples of saccharides that are applicable to the mucosa of a living body include sucrose, lactulose, lactose, maltose, trehalose, cellobiose, cellulose, hemicellulose, microcrystalline cellulose, hydroxypropyl methylcellulose, hydroxypropyl cellulose, starch, pregelatinized starch, amylose, pectin, glycomannan, pullulan, chitosan, chitin, mannitol, lactitol, sorbitol, xylitol, chondroitin acid, heperan acid, and hyaluronic acid. Saccharides are not particularly limited, and cellulose is preferably used from the viewpoint of retaining the olfactory region powder preparation in the nasal cavity for a long period of time.

Examples of amino acids that are applicable to the mucosa of a living body include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

The olfactory region powder preparation may contain an additive in addition to the active ingredient and the base. Examples of the additive include lubricants, fluidizers, binders, solubilizers, buffers, stabilizers, surfactants, preservatives, reducing agents, antioxidants, sweeteners, and flavoring agents that are applicable to the mucosa of a living body. The additives may be used singly or in combinations of two or more.

The olfactory region powder preparation may be filled into a cartridge. A cartridge commonly known in the art can be used. The cartridge may be detachably attached to a sprayer to organize a device. Examples of the sprayer include a single-use sprayer and a multiple-use sprayer. The sprayer is preferably configured to be capable of achieving the above maximum air pressure, maximum air pressure reaching time, and constant air pressure continuous delivery time ($\geq 10$ kPa).

Examples of the device include one having a nozzle part, a preparation filling or loading part, a valve part, and an air generating part.

Examples of the nozzle part include one having a nozzle outer diameter that enables insertion into a human nostril, a nozzle length that allows the nozzle tip to reach the vicinity of the entrance of the nasal cavity, and a nozzle outlet diameter of about 1 to 5 mm.

Examples of the preparation filling or loading part include one having an internal volume (e.g., 0.05 to 2 mL) that enables at least a single dose of the powder preparation to be filled, and one that can be loaded with a container or the like filled with at least a single dose of the powder preparation. The preparation filling or loading part may be integrated with the nozzle part.

Examples of the valve part include one having a flow regulating function (e.g., a swirl flow creating function) for efficiently delivering the preparation present in the preparation filling or loading part, and one having a function to open the valve at a certain pressure.

Examples of the air generating part include a syringe-type air generating part and a pump-type air generating part. Examples of the syringe-type air generating part include one that generates air by pushing a plunger. Examples of the pump-type air generating part include one that generates air by pressing a pump. Also, examples of the air generating part include one in which a canister is filled with propellant gas. The pressure generated in the air generating part may be, for example, 5 to 100 kPa. The amount of air generated in the air generating part may be, for example, 1 to 20 mL.

Preferably 5 to 100 mg, more preferably 5 to 50 mg, and further preferably 10 to 25 mg of the olfactory region powder preparation is delivered into one nostril per time.

Preferably 0.001 to 25 mg, more preferably 0.1 to 20 mg, and further preferably 0.2 to 10 mg of the active ingredient contained in the olfactory region powder preparation is delivered into one nostril per time.

Examples of the method for producing the olfactory region powder preparation include a pressure mixing method involving a mortar or the like; a container mixing method involving a V-type mixer or the like; a freeze drying method involving a shelf-type freeze dryer, a tube-type freeze dryer, a micro-spray freeze dryer, a spray-type freeze dryer, or an agitation-type freeze dryer; a granulation method involving an extrusion granulator, a fluidized bed granulator, or an agitation granulator; a kneading method; and a spray drying method. For example, a sieve; an air sifter; or a crusher such as a hammer mill, a jet mill, or a pin mill may be used to regulate the particle diameter of the olfactory region powder preparation. The above production methods may be used singly or in combinations of two or more.

<Respiratory Region Powder Preparation>

One embodiment of the present invention relates to a powder preparation for selectively administering an active ingredient to a respiratory region in a nasal cavity, the powder preparation containing the active ingredient and having a bulk density of 0.2 to 1.1 g/cm$^3$ and a Hausner ratio of 1.0 to 2.2.

The respiratory region has a reticulately developed vascular system and thus superior absorption of an active ingredient and, also, the hepatic first-pass effect can be avoided by passing through the respiratory region. Accordingly, selectively administering an active ingredient to the respiratory region enables the active ingredient to efficiently circulate the entire body. As a result, systemic diseases can be effectively prevented and/or treated.

The respiratory region has nasopharynx-related lymphoid tissue that is important for antigen uptake, and thus infections can also be effectively prevented and/or treated by selectively administering a vaccine as an active ingredient to the respiratory region.

The term respiratory region is commonly used in the art (e.g., Der Pharmacia Sinica, 2011, 2(3): 94-106). Herein, specifically, the respiratory region means a region that is within the range from the nasal valve located in the anterior part of the nasal cavity to just before the pharyngeal orifice of the eustachian tube located in the posterior part of the nasal cavity and that consists of a portion from the lower part of the olfactory region covering the middle turbinate and the inferior turbinate to the lowermost part of the nasal cavity and a septum-side portion facing it.

Selective administration to the respiratory region means that preferably 50% by weight or more, more preferably 70% by weight or more, further preferably 80% by weight or more, and particularly preferably 90% by weight or more of the active ingredient delivered into the nasal cavity is distributed in the respiratory region. There is no particular upper limit, and the upper limit may be, for example, 100% by weight, 95% by weight, or 90% by weight.

In the case of selective administration to the respiratory region, preferably 0 to 5% by weight, more preferably 0 to 3% by weight, further preferably 0 to 2% by weight, and particularly preferably 0 to 1% by weight of the active ingredient delivered into the nasal cavity is distributed in the olfactory region. The amount of the active ingredient distributed in the respiratory region and the olfactory region can be measured according to the method involving a human nasal cavity model described in the following Examples.

The bulk density of the respiratory region powder preparation is 0.2 to 1.1 g/cm$^3$, preferably 0.2 to 0.8 g/cm$^3$, more preferably 0.2 to 0.7 g/cm$^3$, further preferably 0.2 to 0.6 g/cm$^3$, even more preferably 0.2 to 0.5 g/cm$^3$, and particularly preferably 0.25 to 0.4 g/cm$^3$. The bulk density can be measured according to the method described in the following Examples. The bulk density indicates the specific gravity of the respiratory region powder preparation. When the bulk density is at the above value, the respiratory region selectivity of the active ingredient is improved. The respiratory region powder preparation preferably has a higher bulk density than the olfactory region powder preparation described above.

The Hausner ratio of the respiratory region powder preparation is 1.0 to 2.2, preferably 1.1 to 2.2, more preferably 1.2 to 2.2, further preferably 1.3 to 2.2, even more preferably 1.4 to 2.1, and particularly preferably 1.5 to 2.0. The Hausner ratio can be measured according to the method described in the following Examples. The Hausner ratio indicates the aggregability of the respiratory region powder preparation. When the Hausner ratio is at the above value, the respiratory region selectivity of the active ingredient is improved.

Conventional nasal powder preparations generally have high flowability. On the other hand, the respiratory region powder preparation according to one embodiment of the present invention has a lower flowability than conventional preparations. Due to the low-flowability characteristics, the respiratory region selectivity of the active ingredient is improved. The respiratory region powder preparation preferably has a higher flowability than the olfactory region powder preparation described above. Poor flowability can also be expressed as having high aggregability or low dispersibility.

The tap density of the respiratory region powder preparation is preferably 0.2 to 1.0 g/cm$^3$, preferably 0.2 to 0.8 g/cm$^3$, more preferably 0.3 to 0.9 g/cm$^3$, further preferably 0.4 to 0.7 g/cm$^3$, and particularly preferably 0.4 to 0.6 g/cm$^3$. The tap density can be measured according to the method described in the following Examples. When the tap density is at the above value, the respiratory region selectivity of the active ingredient is improved.

The specific surface area of the respiratory region powder preparation is preferably 0.2 to 2.5 m$^2$/g, more preferably 0.2 to 2.4 m$^2$/g, further preferably 0.2 to 2.2 m$^2$/g, and particularly preferably 0.3 to 2.1 m$^2$/g. The specific surface area can be measured according to the method described in the following Examples. When the specific surface area is at the above value, the respiratory region selectivity of the active ingredient is improved.

The average particle diameter of the respiratory region powder preparation is preferably 10 to 500 μm, more preferably 10 to 300 μm, further preferably 15 to 250 μm, even more preferably 15 to 200 μm, and particularly preferably 15 to 150 μm. The average particle diameter can be measured according to the method described in the following Examples. When the average particle diameter is at the above value, the respiratory region selectivity of the active ingredient is improved.

The respiratory region powder preparation is preferably delivered into the nasal cavity at a predetermined air pressure. The maximum air pressure for delivering the respiratory region powder preparation into the nasal cavity is preferably 5 to 50 kPa, more preferably 5 to 40 kPa, further preferably 5 to 30 kPa, and particularly preferably 5 to 20 kPa. The maximum air pressure can be measured according to the method described in the following Examples. When the maximum air pressure is at the above value, the respiratory region selectivity of the active ingredient is improved.

The maximum air pressure reaching time is preferably 0 to 150 msec, more preferably 0 to 130 msec, further preferably 5 to 120 msec, and particularly preferably 10 to 120 msec. The maximum air pressure reaching time can be measured according to the method described in the following Examples. When the maximum air pressure reaching time is at the above value, the respiratory region selectivity of the active ingredient is improved.

The time of continuous delivery at an air pressure of 5 kPa or more (hereinafter referred to as the "constant air pressure continuous delivery time (≥5 kPa)") is preferably 30 to 200 msec, more preferably 30 to 150 msec, further preferably 40 to 150 msec, and particularly preferably 60 to 150 msec. The constant air pressure continuous delivery time (≥5 kPa) can be measured according to the method described in the following Examples. When the constant air pressure continuous delivery time (≥5 kPa) is at the above value, the respiratory region selectivity of the active ingredient is improved.

The respiratory region powder preparation is preferably delivered at a lower air pressure and in a longer period of time than the olfactory region powder preparation described above.

The administration target of the respiratory region powder preparation is not particularly limited, and is preferably a human. The respiratory region powder preparation is suitable for selectively administering an active ingredient to the respiratory region, especially in the human nasal cavity structure.

The respiratory region powder preparation enables the active ingredient to effectively circulate the entire body, and is thus effective for preventing and/or treating systemic diseases, or performing an examination or diagnosis or a pre-operative or pre-examination treatment. Examples of systemic diseases include defervescence, analgesia, inflammation, rheumatism, hypnosis/sedation, anxiety, psychosis, depression, epilepsy, Parkinson's disease/syndrome, cerebral circulatory metabolism, muscle relaxation, autonomic neuropathy, dizziness, migraine, hypertension, angina, arrhythmia, cardiovascular diseases, allergies, bronchodilation/asthma, other respiratory diseases (such as antitussive and expectorant), peptic ulcer, other gastrointestinal disorders (such as antidiarrhea, intestinal regulation, stomachic, digestion promotion, and catharsis), gout/hyperuricemia, dyslipidemia, diabetes, hormone related diseases (diseases relating to pituitary hormones, corticosteroids, sex hormones, other hormones, and the like), uterine related diseases, osteoporosis/bone metabolism diseases, vitamin deficiency, malnutrition, poisoning (including detoxification), cancer, hyperimmunity, otorhinolaryngology related diseases, mouth related diseases, urinary/genital diseases, hemorrhoids, skin diseases, hematopoiesis/blood coagulation related diseases, narcotic dependence, anesthesia, lifestyle related diseases, life improvement (Kampo), and other examinations/diagnoses (such as imaging and radioactive labeling). Examples of the examination or diagnosis or the pre-operational or pre-examination treatment include imaging, anesthesia, sedation, analgesia, and antianxiety.

Examples of the modality of the active ingredient of the respiratory region powder preparation include, but are not particularly limited to, low molecule compounds, middle molecule drugs including peptide drugs, protein medicaments including antibody medicaments, nucleic acid medicaments, cellular medicaments, regenerative medicine, and vaccine antigens including peptide antigens.

The respiratory region powder preparation is also effective for preventing and/or treating infections. Examples of infections include vaccine/toxoid, bacterial or fungal infections, viral infections, parasitic/protozoal infections, and cancer. Infections and systemic diseases are not completely distinguished, and some may overlap.

Examples of the active ingredient of the respiratory region powder preparation include, but are not particularly limited to, components effective for preventing and/or treating systemic diseases and/or infections. Examples of the active ingredient include tissue plasminogen activators, edaravone, ozagrel sodium, selective thrombin inhibitors, vidarabine, acyclovir, ganciclovir, valganciclovir, zidovudine, didanosine, zalcitabine, nevirapine, delavirdine, saquinavir, ritonavir, indinavir, nelfinavir, vancomycin, ceftazidime, ampicillin, panipenem-betamipron, dexamethasone, cisplatin, carboplatin, vincristine, cyclophosphamide, ifosfamide, temozolomide, etoposide, L-dopa, adrenaline, amphetamine, apomorphine, amantadine, cabergoline, zonisamide, droxidopa, piperiden, phenobarbital, phenytoin, primidone, ethosuximide, zonisamide, clonazepam, midazolam, remimazolam, sodium valproate, carbamazepine, gabapentin, topiramate, cannabide, donepezil, rivastigmine, galantamine, memantine, dimethyl fumarate, natalizumab, haloperidol, spiperone, fluphenazine, chlorpromazine, risperidone, blonanserin, quetiapine, olanzapine, aripiprazole, brexpiprazole, triazolam, zopiclone, zolpidem, etizolam, lormetazepam, bromvalerylurea, chloral hydrate, pentobarbital, rilmazaphone, oxytocin, vasopressin, desmopressin, granisetron, ondansetron, tropisetron, palonosetron, indisetron, triazolam, melatonin, levetiracetam, cannabinoid, clonazepam, diazepam, nitrazepam, zorbidem, midazolam, remimasazolam, donepezil, memantine, tiapride, cefaclor, enoxacin, acyclovir, zidovudine, didanosine, nevirabine, indinavir, dantrolene, digoxin, trihexyphenidyl, piperidene, dextromethorphan, naloxone, betahistine, naphazoline, diltiazem, tranilast, loperamide, beclomethasone, chlorpheniramine, sildenafil, tadalafil, vardenafil, cyanocobalamin, finasteride, epinephrine, oxybutynin, propiverine, solifenacin, tolterodine, imidafenacin, fesoterodine, mirabegron, tamsulosin, silodosin, 5-FU, telaprevir, ribavirin, simeprevir, guanfasin, methylphenidate, atomoxetine, progesterone, sumatriptan, zolmitriptan, dihydroergotamine, rizatriptan, erenumab, galcanezumab, fremanezumab, fomivirsen, mipomersen, nusinersen, cyclosporine, tacrolimus, fluorodeoxyglucose, fluorothymidine, iopamidol, thallium, manganese, technesium, insulin, growth hormone, growth hormone releasing peptide, ghrelin, glucagon, calcitonin, interferon, erythropoietin, interleukin, PTH (1-84), PTH (1-34), PTH-related peptide, GLP-1, vasopressin, leuprorelin, granulocyte colony stimulating factor, prolactin, menopausal gonadotropic hormone, placental gonadotropic Snbl2600 hormone, follicle stimulating hormone, luteinizing hormone, leptin, nerve growth factor (NGF), stem cell growth factor (SCGF), keratinocyte growth factor (KGF), low molecular weight heparin, tacrolimus, allergen extract powder, antibody drugs including human antibodies (such as adalimumab, panitumumab, golimumab, canakinumab, ofatumumab, denosumab, ipilimumab, berimumab, laxibacumab, ramucirumab, nivolumab, secukinumab, evolocumab, alirocumab, nesitumumab, nivolumab, and pembrolizumab), chimeric antibody abciximab, humanized antibody bevacizumab, mouse antibody burinatumomab, and salts thereof. The active ingredients may be used singly or in combinations of two or more.

Moreover, examples of the active ingredient include vaccine antigens to the following viruses and pathogens. Examples of viruses and pathogens include adenovirus, AIDS virus, baculovirus, HCMV (human cytomegalovirus), hemorrhagic fever virus, hepatitis virus, herpes B virus, immunodeficiency virus, human immunodeficiency virus, human T-cell leukemia virus, neonatal gastroenteritis virus, infectious hematopoietic necrosis virus, infectious pancreatic necrosis virus, influenza virus, Japanese encephalitis virus, leukemia virus, mumps virus, orthomyxovirus, pneumonia virus, poliovirus, polydnavirus, rotavirus, SARS virus, vaccinia virus, RS virus, *Shigella* species, *Salmonella typhi, Mycobacterium tuberculosis, Clostridium tetani, Corynebacterium diphtheriae, Neisseria meningitidis, Bordetella pertussis, Streptococcus pneumonia, Bacillus anthracis, Clostridium botulinum, Clostridium difficile, Clostridium perfringens, Enterococcus faecalis, Enterococcus fascium, Haemophilus influenzae, Helicobacter pylori, Mycobacterium leprae, Neisseria gonorrhoeae, Neisseria meningitidis, Salmonella typhi, Staphylococcus aureus, Treponema pallidum, Vibrio cholerae*, and *Plasmodium falciparum*. The active ingredients may be used singly or in combinations of two or more.

The respiratory region powder preparation may contain a base in addition to the active ingredient. Examples of the base include saccharides and amino acids that are applicable to the mucosa of a living body. The bases may be used singly or in combinations of two or more.

Examples of saccharides that are applicable to the mucosa of a living body include sucrose, lactulose, lactose, maltose, trehalose, cellobiose, cellulose, hemicellulose, microcrystalline cellulose, hydroxypropyl methylcellulose, hydroxypropyl cellulose, starch, pregelatinized starch, amylose, pectin, glycomannan, pullulan, chitosan, chitin, mannitol, lactitol, sorbitol, xylitol, chondroitin acid, heperan acid, and hyaluronic acid. Saccharides are not particularly limited, and cellulose is preferably used from the viewpoint of retaining the respiratory region powder preparation in the nasal cavity for a long period of time.

Examples of amino acids that are applicable to the mucosa of a living body include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

The respiratory region powder preparation may contain an additive in addition to the active ingredient and the base. Examples of the additive include lubricants, fluidizers, binders, solubilizers, buffers, stabilizers, surfactants, preservatives, reducing agents, antioxidants, sweeteners, flavoring agents, and adjuvants that are applicable to the mucosa of a living body. The additives may be used singly or in combinations of two or more.

The respiratory region powder preparation may be filled into a cartridge. A cartridge commonly known in the art can be used. The cartridge may be detachably attached to a sprayer to organize a device. Examples of the sprayer include those similar to the sprayers described in relation to the above olfactory region powder preparation. The sprayer is preferably configured to be capable of achieving the above maximum air pressure, maximum air pressure reaching time, and constant air pressure continuous delivery time (≥5 kPa).

Preferably 5 to 100 mg, more preferably 5 to 50 mg, and further preferably 10 to 25 mg of the respiratory region powder preparation is delivered into one nostril per time.

Preferably 0.001 to 25 mg, more preferably 0.1 to 20 mg, and further preferably 0.2 to 10 mg of the active ingredient contained in the respiratory region powder preparation is delivered into one nostril per time.

Examples of the method for producing the respiratory region powder preparation include a pressure mixing method involving a mortar or the like; a container mixing method involving a V-type mixer or the like; a freeze drying method involving a shelf-type freeze dryer, a tube-type freeze dryer, a micro-spray freeze dryer, a spray-type freeze dryer, or an agitation-type freeze dryer; a granulation method involving an extrusion granulator, a fluidized bed granulator, or an agitation granulator; a kneading method; and a spray drying method. For example, a sieve; an air sifter; or a crusher such as a hammer mill, a jet mill, or a pin mill may be used to regulate the particle diameter of the respiratory region powder preparation. The above production methods may be used singly or in combinations of two or more.

EXAMPLES

Below, the present invention will now be described in more detail by way of Examples and Comparative Examples, but the technical scope of the present invention is not limited thereto.

1. Preparation of Powder Preparations

Test preparations having the compositions shown in Table 1 were prepared. The materials and the production methods of the test preparations are as described below.

(Material: Active ingredients)

Tartrazine (Wako Pure Chemical Industries, Ltd.), manganese(II) chloride tetrahydrate (Sigma-Aldrich Co., LLC), ovalbumin (Sigma-Aldrich Co., LLC), thymidine (Wako Pure Chemical Industries, Ltd.), testosterone (Wako Pure Chemical Industries, Ltd.), oxytocin (Sigma-Aldrich Co., LLC), indomethacin (Wako Pure Chemical Industries, Ltd.).

(Material: Excipients)

Ceolus(R) PH-301 (Asahi Kasei Chemicals Corporation), Ceolus(R) PH-F20JP (Asahi Kasei Chemicals Corporation), tricalcium phosphate (ICL Performance Products LP), sodium chloride (Wako Pure Chemical Industries, Ltd.), mannitol (Wako Pure Chemical Industries, Ltd.), trehalose dihydrate (Wako Pure Chemical Industries, Ltd.), pullulan (Tokyo Chemical Industry Co., Ltd.), Respitose SV003 (DEF Pharma), light anhydrous silicic acid (Fuji Silysia Chemical Ltd.), HPMC TC-5E (Shin-Etsu Chemical Co., Ltd.), pregelatinized starch (Asahi Kasei Chemicals Corporation).

(Production Method: Mortar Mixing)

Components shown in Table 1 were placed in a glass mortar in a composition ratio shown in Table 1 and mixed for about 10 minutes.

(Production Method: Freeze Drying (Vial))

Components shown in Table 1 were admixed into a phosphate buffer in a composition ratio shown in Table 1, and then the admixture was placed in 1 mL glass vial and placed in a shelf-type freeze dryer (FreeZone Triad Freeze Dry System, Labconco Corp.) to give a freeze-dried product under the following conditions. As for the freeze-drying conditions, preliminary freezing was performed at −30° C. for 1.5 hours, freezing was performed at −45° C. for 0.6 hours, then primary drying was performed at −45° C. for 0.4 hours and −35° C. for 14.5 hours and, moreover, secondary drying was performed at 30° C. for 4 hours, under a reduced pressure of 105 mTorr. The prepared freeze-dried product was crushed with a Vortex to give a test preparation.

(Production Method: Freeze Drying (Tray))

Ultrapure water was placed in a 200 mL aluminum tray in advance, the bottom part inside the aluminum tray was frozen at −20° C., then components shown in Table 1 were admixed into a phosphate buffer in a composition ratio shown in Table 1, and the admixture was placed in the aluminum tray, pre-frozen at −20° C. for 2 hours, and placed in a shelf-type freeze dryer (FreeZone Triad Freeze Dry System, Labconco Corp.) to give a freeze-dried product under the following conditions. As for the freeze-drying conditions, primary drying was performed at −25° C. for 30 hours and, moreover, secondary drying was performed at 30° C. for 37 hours, under a reduced pressure of 105 mTorr. The prepared freeze-dried product was crushed with Fine Impact Mill 100UPZ-C (Hosokawa Micron Co., Ltd.) to give a test preparation.

(Production Method: Freeze Drying (Tube))

Components shown in Table 1 were placed in a 2000 mL glass container in a composition ratio shown in Table 1, the liquid volume was adjusted with a phosphate buffer, and the admixture was placed in a tube-type freeze dryer (Model ICS-1-301, Kyowa Vacuum Technology Co., Ltd.) to give a freeze-dried product under the following conditions. As for the freeze-drying conditions, freezing was performed at −45° C. for 2 hours, then primary drying was performed at −25° C. for 30 hours and, moreover, secondary drying was performed at 30° C. for 13 hours, under a reduced pressure of 6.7 Pa. The prepared freeze-dried product was crushed with Fine Impact Mill 100UPZ-C (Hosokawa Micron Co., Ltd.) to give a test preparation.

(Production Method: Micro-Spray Freeze Drying)

Components shown in Table 1 were placed in a 1000 mL glass container in a composition ratio shown in Table 1, the liquid volume was adjusted with a phosphate buffer, and the admixture was placed in a micro-spray freeze dryer (μPD400, ULVAC Inc.) to give a freeze-dried product under the following conditions. As for the freeze-drying conditions, spray-freezing was performed at a shelf temperature of −40° C., dried under reduced pressure of 10 Pa at 30° C. for 16 hours and then dried at Full Vacuum. The prepared freeze-dried product was directly used as a test preparation.

(Production Method: Container Mixing)

Components shown in Table 1 were placed in a glass container in a composition ratio shown in Table 1 and vortex-mixed for about 10 minutes.

(Production Method: Fluidized-Bed Granulation)

Components other than HPMC or starch shown in Table 1 were placed in a fluidized-bed granulator (FL-LABO, Freund Corporation) in a composition ratio shown in Table 1, and, while causing the powder in the granulator to flow by air at 70° C., a 5.7% solution of HPMC in purified water or a 1.4% solution of starch in purified water was sprayed into the granulator. The prepared granulated product was directly used as a test preparation.

TABLE 1

Composition and production method of powder preparations

Blending component (blending w/w %)

| | Active ingredient | Excipient | Production method |
|---|---|---|---|
| Test preparation 1 | Tartrazine (5%) | MCC-1 (95%) | Mortar mixing |
| Test preparation 2 | Tartrazine (5%) | MCC-2 (95%) | Mortar mixing |
| Test preparation 3 | Tartrazine (5%) | MCC-1 (10%), MCC-2 (84.2%), TCP (0.8%) | Mortar mixing |
| Test preparation 4 | Mn (0.4%) | MCC-1 (10%), MCC-2 (88.8%), TCP (0.8%) | Mortar mixing |
| Test preparation 5 | OVA (8%) | MCC-1 (10%), MCC-2 (81.2%), TCP (0.8%) | Mortar mixing |
| Test preparation 6 | Thymidine (5%) | MCC-1 (10%), MCC-2 (84.2%), TCP (0.8%) | Mortar mixing |
| Test preparation 7 | Tartrazine (5%) | NaCl (95%) | Mortar mixing |
| Test preparation 8 | Tartrazine (5%) | MNT (95%) | Mortar mixing |
| Test preparation 9 | Testosterone (5%) | MNT (95%) | Mortar mixing |
| Test preparation 10 | Oxytocin (0.4%) | MNT (99.6%) | Mortar mixing |
| Test preparation 11 | Tartrazine (5%) | THL (95%) | Mortar mixing |
| Test preparation 12 | Tartrazine (5%) | PLN (95%) | Mortar mixing |
| Test preparation 13 | Tartrazine (5%) | LCT (95%) | Mortar mixing |
| Test preparation 14 | Tartrazine (5%) | ASA (95%) | Mortar mixing |
| Test preparation 15 | — | MCC-2 (50%), THL (50%) | Freeze drying (vial) |
| Test preparation 16 | — | MCC-2 (75%), THL (25%) | Freeze drying (vial) |
| Test preparation 17 | Tartrazine (5%) | MCC-2 (47.5%), THL (47.5) | Freeze drying (tray) |
| Test preparation 18 | OVA (8%) | MCC-2 (46%), THL (46%) | Freeze drying (tray) |
| Test preparation 19 | Tartrazine (5%) | MCC-2 (47.5%), THL (47.5%) | Freeze drying (tube) |
| Test preparation 20 | — | MCC-2 (50%), THL (50%) | Micro-spray freeze drying |
| Test preparation 21 | Tartrazine (5%) | MCC-1 (84.2%), MCC-2 (10%), TCP (0.8%) | Container mixing |
| Test preparation 22 | Testosterone (10%) | MCC-1 (79.2%), MCC-2 (10%), TCP (0.8%) | Container mixing |
| Test preparation 23 | Tartrazine (20%) | NaCl (80%) | Container mixing |
| Test preparation 24 | Tartrazine (15%) | MNT (85%) | Container mixing |
| Test preparation 25 | Indomethacin (2.5%) | MCC-2 (68.5%), MNT (25%), HPMC (4%) | Fluidized-bed granulation |
| Test preparation 26 | Indomethacin (2.5%) | MCC-2 (70.5%), MNT (25%), Starch (2%) | Fluidized-bed granulation |
| Test preparation 27 | Oxytocin (8%) | MCC-1 (10%), MCC-2 (81.2%), TCP (0.8%) | Mortar mixing |
| Test preparation 28 | Testosterone (5%) | NaCl (95%) | Mortar mixing |

Mn: Manganese(II) chloride tetrahydrate
OVA: Ovalbumin
MCC-1: Crystalline cellulose (Ceolus ® PH-301)
MCC-2: Crystalline cellulose (Ceolus ® PH-F20JP)
TCP: Tricalcium phosphate
NaCl: Sodium chloride
MNT: Mannitol
THL: Trehalose dihydrate
PLN: Pullulan
LCT: Lactose (Respitose SV003)
ASA: Light anhydrous silicic acid
HPMC: Hydroxypropyl methylcellulose (HPMC TC-5E)
Starch: Pregelatinized starch 2. Physical Properties of Powder Preparations The specific surface area, average particle diameter, bulk density, tap density, and Hausner ratio of the test preparations shown in Table 1 were measured. The measurement methods of the respective physical properties are as described below. The results are shown in Table 2.

(Specific Surface Area)

The measurement sample was dried at 100° C. for 1 hour under suction reduced pressure or at room temperature for 16 hours under suction reduced pressure, and measured with a specific surface area analyzer based on a gas adsorption method involving nitrogen or krypton gas (Autosorb-iQ-MP, Quantachrome Instruments, or ASAP2460, Micromeritics Instrument Corporation).

(Average Particle Diameter)

The average primary particle diameter was measured under a dispersion pressure of 2 bar with a particle size distribution analyzer based on a laser diffraction method (Mastersizer 2000, Malvern).

(Bulk Density)

Based on the powder property measurement method of the Japanese Pharmacopoeia General Testing Method, the volume when each powder preparation having a known mass was placed in a graduated cylinder was measured, and the bulk density was calculated by dividing the mass by the volume.
(Tap Density)
Based on the powder property measurement method of the Japanese Pharmacopoeia General Testing Method, each powder preparation having a known mass was placed in a graduated cylinder, then the graduated cylinder was tapped, the volume at which no more volume change of the powder preparation was recognized was measured, and the tap density was calculated by dividing the mass by the volume.
(Hausner Ratio)
The Hausner ratio was calculated by dividing the bulk density by the tap density.

sure buildup was measured. From the measured pressure change data, the maximum air pressure, the maximum air pressure reaching time, and the constant air pressure continuous delivery time (≥10 kPa or ≥5 kPa) were calculated.
(Measurement of Delivered Rate)
The device in which 20 mg or 25 mg of a test preparation was filled into the preparation filling part was weighed, then the air generating part was operated, and the sprayer was weighed again. The delivered rate was calculated from the difference between the weights of the device before and after delivery.
(Measurement of Distribution Ratio in Olfactory Region)
A human nasal cavity model (FIG. 1) was created using a 3D printer based on head CT scan data of a Japanese adult

TABLE 2

Physical properties of test preparations

|  | Specific surface area (m²/g) | Average particle diameter (μm) | Bulk density (g/cm³) | Tap density (g/cm³) | Hausner ratio |
|---|---|---|---|---|---|
| Test Preparation 1 | — | 67 | 0.38 | 0.57 | 1.51 |
| Test Preparation 2 | — | 17 | 0.24 | 0.45 | 1.90 |
| Test Preparation 3 | 2.28 | 15 | 0.23 | 0.47 | 2.07 |
| Test Preparation 4 | — | 19 | 0.26 | 0.48 | 1.81 |
| Test Preparation 5 | — | 19 | 0.24 | 0.50 | 2.10 |
| Test Preparation 6 | — | 16 | 0.27 | 0.53 | 1.92 |
| Test Preparation 7 | 0.17 | 489 | 1.05 | 1.33 | 1.27 |
| Test Preparation 8 | 0.41 | 17 | 0.41 | 0.74 | 1.80 |
| Test Preparation 9 | — | 23 | 0.44 | 0.71 | 1.64 |
| Test Preparation 10 | — | 20 | 0.43 | 0.71 | 1.64 |
| Test Preparation 11 | 2.11 | 242 | 0.62 | 0.80 | 1.29 |
| Test Preparation 12 | — | 283 | 0.31 | 0.40 | 1.29 |
| Test Preparation 13 | 0.78 | 61 | 0.58 | 0.83 | 1.43 |
| Test Preparation 14 | 238.18 | 3 | 0.07 | 0.09 | 1.33 |
| Test Preparation 15 | 0.57 | — | — | — | — |
| Test Preparation 16 | 0.64 | — | — | — | — |
| Test Preparation 17 | 1.41 | 32 | 0.28 | 0.48 | 1.71 |
| Test Preparation 18 | — | 48 | 0.32 | 0.56 | 1.72 |
| Test Preparation 19 | 0.92 | 34 | 0.33 | 0.53 | 1.63 |
| Test Preparation 20 | — | 535 | 0.12 | 0.13 | 1.06 |
| Test Preparation 21 | — | 17 | 0.23 | 0.48 | 2.10 |
| Test Preparation 22 | — | 19 | 0.24 | 0.53 | 2.16 |
| Test Preparation 23 | — | 526 | 1.00 | 1.05 | 1.05 |
| Test Preparation 24 | — | 21 | 0.43 | 0.71 | 1.64 |
| Test Preparation 25 | 0.92 | 41 | 0.28 | 0.40 | 1.44 |
| Test Preparation 26 | 0.99 | 82 | 0.26 | 0.36 | 1.36 |
| Test Preparation 27 | 2.155 | 19 | 0.21 | 0.38 | 1.85 |
| Test Preparation 28 | 0.283 | 458 | 1.02 | 1.03 | 1.01 |

3. Distribution Evaluation of Test Preparations
(Device)

Figure 2:
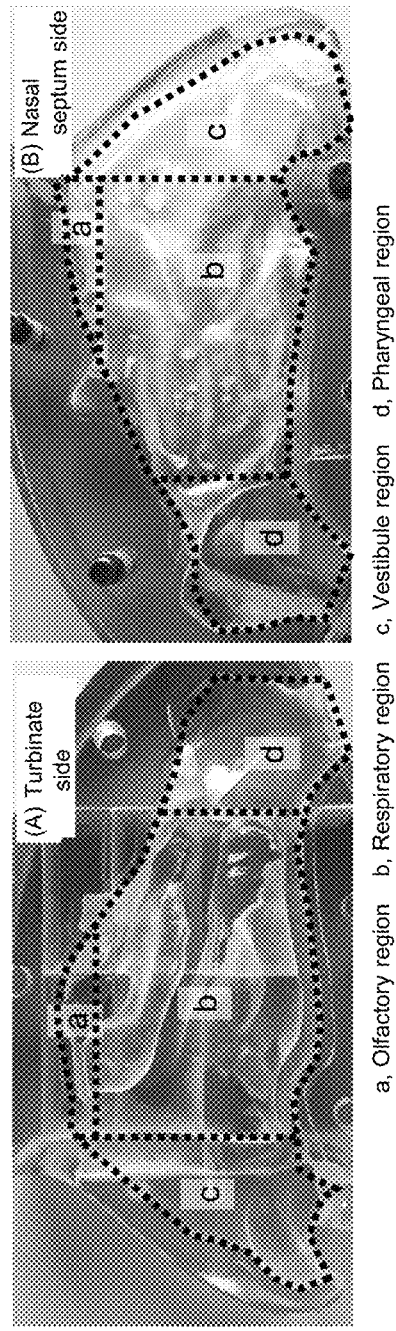
FIG. 2 shows various regions (a: olfactory region, b: respiratory region, c: vestibule region, d: pharyngeal region) in the nasal cavity (A: turbinate side, B: nasal septum side) in a human nasal cavity model.
Figure 3:
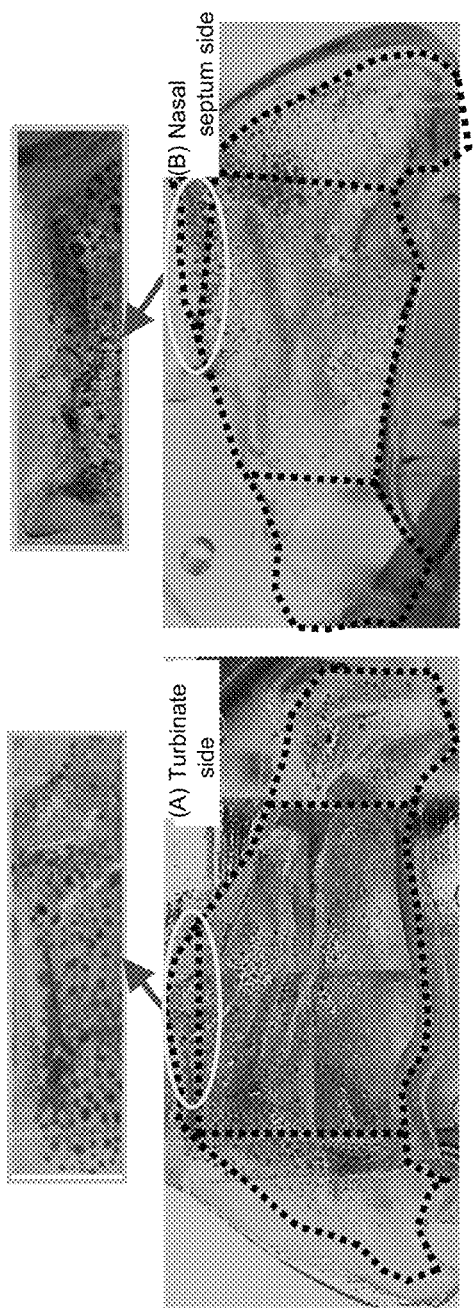
FIG. 3 shows the distribution of a test preparation in the nasal cavity model.

A device was fabricated to which a nozzle part (this may also serve as an preparation filling part), an preparation filling part, a valve part, and an air generating part were connected in this order. The air generating part is a syringe type or a pump type and is capable of controlling, within a certain range, the properties (including the maximum air pressure, the maximum air pressure reaching time, and the constant air pressure continuous delivery time (≥10 kPa or ≥5 kPa)) of blast air to be generated including adjustment of the valve opening timing.
(Measurement of Blast Air Properties)
A pressure gauge connected to a data logger was attached to the air generating part of the device, and the pressure change every 1 msec when the air generating part was operated was measured. When discharging blast air by opening the valve from a pressurized state, pressure change data until a pressure buildup was complete was not collected, and the pressure change after completion of a presmale. In this human nasal cavity model, the right and left nasal cavities can be separated from the nasal septum, making it possible to easily observe the distribution of a preparation delivered into the nasal cavity model and wash off and recover the preparation. The regions in the nasal cavity are shown in FIG. 2. As is clear from FIG. 2, the olfactory region is a very limited region. 25 mg of a tartrazine-containing test preparation was filled into the preparation filling part of the device, the nozzle part thereof was inserted into one nostril of the human nasal cavity model, the nasal cavity of which was moistened with artificial saliva, and the air generating part was operated to deliver the test preparation into the nasal cavity. After delivery, the human nasal cavity model was disassembled, and the preparation adhered to the olfactory region and the preparation adhered the respiratory region of the human nasal cavity model shown in FIG. 2 were washed off with purified water and recovered (FIG. 3 shows a representative example of the preparation distribution in the human nasal cavity model delivered with the test preparation). The amount of tartrazine in the recovered test preparation was measured by HPLC, and the ratio of tartrazine distributed in the evaluation region was calculated based on the amount of tartrazine delivered from the device, and was regarded as a distribution ratio. The delivered rate was calculated by dividing the total amount of tartrazine recovered from the human nasal cavity model by the theoretical amount of tartrazine filled into the device.

TABLE 3

Results of evaluation of distribution in human nasal cavity model (olfactory region targeting delivery system)

| | | Blast air properties | | | Delivered | |
| | Test Preparation | $P_{max}$ (kPa) | $T_{max}$ (msec) | $T_{d\ of \geq 10\ kPa}$ (msec) | rate (%) | Distribution ratio (%) Olfactory region |
|---|---|---|---|---|---|---|
| Example 1 | Test Preparation 3 | 20 | 0 | 20 | 69.4 | 48.9 |
| Example 2 | Test Preparation 3 | 20 | 0 | 44 | 90.6 | 47.1 |
| Example 3 | Test Preparation 3 | 40 | 0 | 24 | 89.4 | 21.8 |
| Example 4 | Test Preparation 3 | 59 | 0 | 30 | 87.7 | 33.2 |
| Example 5 | Test Preparation 3 | 59 | 0 | 47 | 85.0 | 31.2 |
| Example 6 | Test Preparation 3 | 59 | 0 | 69 | 88.0 | 23.0 |
| Example 7 | Test Preparation 8 | 20 | 0 | 31 | 98.5 | 67.5 |
| Example 8 | Test Preparation 17 | 20 | 0 | 31 | 90.8 | 36.5 |
| Comparative Example 1 | Test Preparation 8 | 250 | 0 | 68 | 80.0 | 17.1 |
| Comparative Example 2 | Test Preparation 7 | 59 | 0 | 47 | 57.1 | 8.8 |
| Comparative Example 3 | Test Preparation 11 | 20 | 0 | 44 | 83.0 | 9.4 |
| Comparative Example 4 | Test Preparation 11 | 40 | 0 | 24 | 86.3 | 12.8 |
| Comparative Example 5 | Test Preparation 11 | 41 | 0 | 61 | 78.8 | 17.0 |
| Comparative Example 6 | Test Preparation 13 | 20 | 0 | 31 | 97.9 | 0.0 |
| Comparative Example 7 | Test Preparation 17 | 26 | 71 | 100 | 84.8 | 6.6 |

$P_{max}$: Maximum air pressure
$T_{max}$: Maximum air pressure reaching time
$T_{d\ of \geq 10\ kPa}$: Constant air pressure continuous delivery time ($\geq 10$ kPa)

(Results of Evaluation of Distribution in Olfactory Region)

As shown in Table 3, in Examples 1 to 8, the delivered rate was 60% or more, and 20% or more of it was distributed in the olfactory region, which is a very limited region. Accordingly, it was found that test preparations 3, 8, and 17 are effective in a delivery system that targets the olfactory region. Also, from the comparison of Examples 1 to 8 and Comparative Examples 2 to 6 having the same or similar blast air properties, it was found that the physical properties of the preparation are important for increasing selectivity for the olfactory region. Moreover, from the comparison of Examples 7 and 8 and Comparative Examples 1 and 7 in which the same test preparations are used, it was found that by adopting the predetermined blast air properties, selectivity for the olfactory region is increased.

TABLE 4

Results of evaluation of distribution in human nasal cavity model (respiratory region targeting delivery system)

| | | Blast air properties | | | Delivered | Distribution ratio (%) | |
| | Test Preparation | $P_{max}$ (kPa) | $T_{max}$ (msec) | $T_{d\ of \geq 5\ kPa}$ (msec) | rate (%) | Olfactory region | Respiratory region |
|---|---|---|---|---|---|---|---|
| Example 9 | Test Preparation 3 | 9 | 53 | 43 | 90.5 | 1.6 | 52.0 |
| Example 10 | Test Preparation 3 | 26 | 71 | 100 | 90.9 | 2.6 | 64.5 |
| Example 11 | Test Preparation 8 | 26 | 71 | 100 | 80.9 | 0.2 | 73.1 |
| Example 12 | Test Preparation 11 | 9 | 53 | 43 | 76.6 | 0.2 | 82.2 |
| Example 13 | Test Preparation 11 | 26 | 71 | 100 | 79.6 | 0.3 | 79.1 |
| Example 14 | Test Preparation 13 | 26 | 71 | 100 | 65.6 | 0.3 | 83.8 |

TABLE 4-continued

Results of evaluation of distribution in human nasal cavity
model (respiratory region targeting delivery system)

| | | Blast air properties | | | Delivered | Distribution ratio (%) | |
|---|---|---|---|---|---|---|---|
| | Test Preparation | $P_{max}$ (kPa) | $T_{max}$ (msec) | $T_{d\ of \geq 5\ kPa}$ (msec) | rate (%) | Olfactory region | Respiratory region |
| Example 15 | Test Preparation 17 | 26 | 71 | 100 | 79.9 | 0.0 | 60.7 |
| Comparative Example 8 | Test Preparation 7 | 26 | 71 | 100 | 58.7 | 0.1 | 15.3 |
| Comparative Example 9 | Test Preparation 11 | 20 | 0 | 31 | 32.8 | 0.0 | 77.6 |
| Comparative Example 10 | Test Preparation 17 | 49 | 329 | 1030 | 84.7 | 0.1 | 43.5 |

$P_{max}$: Maximum air pressure
$T_{max}$: Maximum air pressure reaching time
$T_{d\ of \geq 5\ kpa}$: Constant air pressure continuous delivery time ($\geq 5$ kPa)

(Results of Evaluation of Distribution in Respiratory Region)

As shown in Table 4, in Examples 9 to 15, the delivered rate was 60% or more, and 50% or more of it was distributed in the respiratory region, and distribution in the olfactory region was less than 5%. For selective administration to the respiratory region, distribution in the olfactory region is desirably as small as possible. Accordingly, it was found that test preparations 3, 8, 11, 13, and 17 are effective in a delivery system that targets the respiratory region. Also, from the comparison of Examples 10, 11 and 13 to 15 and Comparative Example 8 having the same blast air properties, it was found that the physical properties of the preparation are important for increasing selectivity for the respiratory region. Moreover, from the comparison of Examples 12, 13 and 15 and Comparative Examples 9 and 10 in which the same test preparations are used, it was found that by adopting the predetermined blast air properties, selectivity for the respiratory region is increased.

4. Nasal Cavity Distribution and Brain Migration Evaluations for Nasal Manganese Preparation in Monkey (Example 16)

25 mg of test preparation 4 shown in Table 1 was injected into the right nasal cavity of a conscious male cynomolgus monkey (body weight 3.73 kg; n=1; SNBL, Ltd.), which has a nasal cavity structure similar to that of a human, with an olfactory region delivery device having an air generating part having a maximum air pressure of 58 kPa, a maximum air pressure reaching time of 0 msec, and a constant air pressure continuous delivery time ($\geq 10$ kPa) of 110 msec. In order to evaluate the nasal cavity distribution and brain migration of manganese contained in the test preparation, manganese-enhanced MRI imaging (MAGNETOM Allegra, 3T, SIEMENS) for the head was performed before administration, immediately after administration, 3 hours after administration, 6 hours after administration, and 24 hours after administration, after inhalation anesthesia immediately before imaging. Images obtained by manganese-enhanced MRI imaging for the head were analyzed with image analysis software OsiriX MD (Version 6.0, 64-bit, Pixmeo SARL). This test was performed after being approved by the Animal Experimentation Ethics Committee of SNBL, Ltd.

Figure 4:
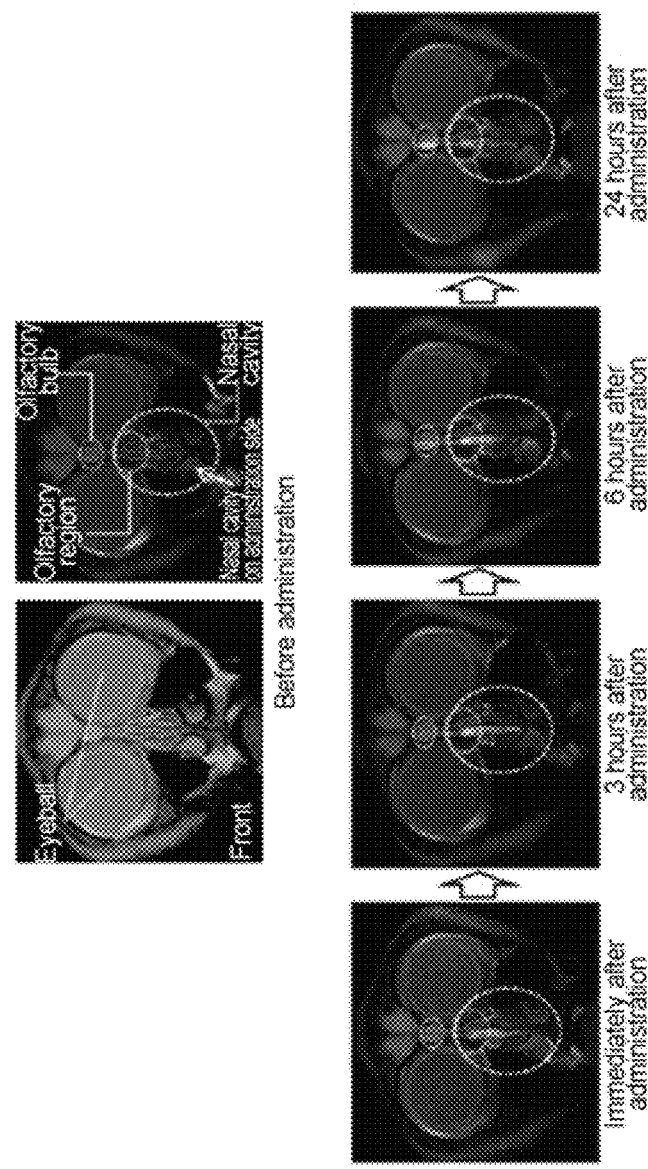
FIG. 4 shows nasal cavity distribution and brain migration of manganese imaged by manganese-enhanced MRI in a monkey.

FIG. 4 shows manganese-enhanced MRI images. FIG. 4 shows that manganese is markedly distributed in the olfactory region in the nasal cavity immediately after administration, and that manganese migrated to the olfactory bulb in the brain 3 hours or later after administration. Accordingly, it was verified that the olfactory region delivery system according to the present invention increases brain migration of the active ingredient.

5. Evaluation of Immunogenicity for Nasal OVA Preparation in Monkey (Example 17)

25 mg of test preparation 5 shown in Table 1 was delivered into the right nasal cavity of male cynomolgus monkeys (body weight 2.8 to 5.5 kg; n=5; SNBL, Ltd.), which have a nasal cavity structure similar to that of a human, with a respiratory region delivery device having an air generating part having a maximum air pressure of 28 kPa, a maximum air pressure reaching time of 88 msec, and a constant air pressure continuous delivery time ($\geq 5$ kPa) of 146 msec, once on the first administration day (day 1), day 15, and day 36, i.e., a total of 3 times. For immunogenicity evaluation, serum and nasal cavity washing fluid were collected 4 days before the first administration day, day 14, day 29, and day 50.

As Comparative Example 11, 25 mg of test preparation 5 shown in Table 1 was delivered into the right nasal cavity of male cynomolgus monkeys (body weight 3.6 to 4.3 kg; n=5; SNBL, Ltd.) with an olfactory region delivery device having an air generating part having a maximum air pressure of 58 kPa, a maximum air pressure reaching time of 0 msec, and a constant air pressure continuous delivery time ($\geq 10$ kPa) of 110 msec, once on the first administration day (day 1), day 15, and day 36, i.e., a total of 3 times. For immunogenicity evaluation, serum and nasal cavity washing fluid were collected 4 days before the first administration day, day 14, day 29, and day 50. This test was performed after being approved by the Animal Experimentation Ethics Committee of SNBL, Ltd.

As for the anti-OVA-IgG antibody titer in the collected serum and the anti-OVA-sIgA antibody titer in the nasal cavity washing fluid, absorbance at 450 nm was measured with a plate reader (F039300, Tecan Japan) based on an ELISA method involving goat anti-monkey IgG (Fc specific) conjugated with horseradish peroxidase (Nordic-MUbio) and goat anti-monkey secretory component (free and bound) conjugated with horseradish peroxidase (Nordic-MUbio), respectively. The value obtained by subtracting the average value of the absorbance of the negative control well from the absorbance of each well was regarded as a measured value, and, in the case of a serum sample, the average value+3 standard deviations (SD) of the measured value of a pre-serum sample that was diluted 500-fold, and in the case of a nasal cavity washing fluid sample, the average value+3 standard deviations (SD) of the measured value of a pre-nasal cavity washing fluid sample that was diluted 10-fold were each regarded as a cut-off value. Measured values higher than the cutoff values were considered to be antibody positive, and the maximum sample dilution ratio thereof was regarded as an antibody titer. When the absorbance of the Pre sample was low, and it was difficult to calculate the antibody titer by the above method, the cutoff value was uniformly set at 0.1 to calculate the antibody titer. The serum sample was treated such that the antibody titer was 250 when less than the detection sensitivity, and the nasal cavity washing fluid sample was treated such that the antibody titer was 5 when less than the detection sensitivity.

Figure 5:
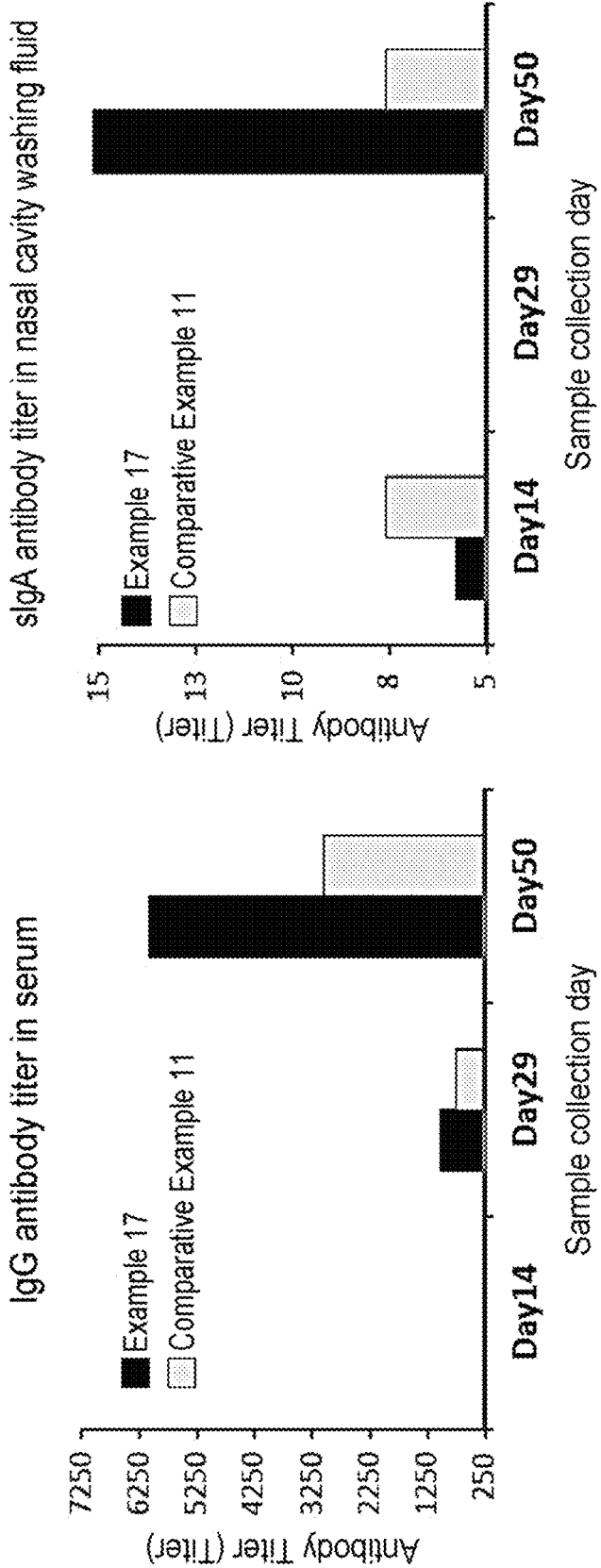
FIG. 5 shows the immunogenicity of OVA antigen after selectively administering an OVA antigen preparation to the respiratory region in the nasal cavity.

The measurement results of the anti-OVA-IgG antibody titer in serum and the anti-OVA-sIgA antibody titer in nasal cavity washing fluid are shown in Table 5 and Table 6, respectively, and both in FIG. 5. As is clear from Tables 5 and 6 and FIG. 5, the IgG antibody titer and the sIgA antibody titer of Example 17 were about twice as high as those of Comparative Example 11 50 days after administration. Accordingly, it was verified that the respiratory region delivery system according to the present invention increases immunogenicity.

TABLE 5

Anti-GVA-TvG antibody titers in serum

| | | Anti-OVA-IgG antibody titer in serum | | |
|---|---|---|---|---|
| | Animal No. | Day 14 | Day 29 | Day 50 |
| Example 17 | 1 | 250 | 2000 | 8000 |
| | 2 | 250 | 500 | 1000 |
| | 3 | 250 | 1000 | 16000 |
| | 4 | 250 | 500 | 4000 |
| | 5 | 250 | 2000 | 16000 |
| | Geometric average | 250 | 1000 | 6063 |
| Comparative Example 11 | 6 | 250 | 500 | 8000 |
| | 7 | 250 | 4000 | 8000 |
| | 8 | 250 | 500 | 1000 |
| | 9 | 250 | 250 | 1000 |
| | 10 | 250 | 1000 | 4000 |
| | Geometric average | 250 | 758 | 3031 |

TABLE 6

Anti-OVA-sIgA antibody titers in nasal cavity washing fluid

| | | Anti-OVA-sIgA antibody titer in nasal cavity washing fluid | | |
|---|---|---|---|---|
| | Animal No. | Day 14 | Day 29 | Day 50 |
| Example 17 | 1 | 5 | 5 | 10 |
| | 2 | 5 | 5 | 5 |
| | 3 | 5 | 5 | 40 |
| | 4 | 5 | 5 | 10 |
| | 5 | 10 | 5 | 40 |
| | Geometric average | 6 | 5 | 15 |
| Comparative Example 11 | 6 | 5 | 5 | 10 |
| | 7 | 10 | 5 | 10 |
| | 8 | 10 | 5 | 10 |
| | 9 | 10 | 5 | 5 |
| | 10 | 5 | 5 | 5 |
| | Geometric average | 8 | 5 | 8 |

6. Evaluation of Absorbability for Nasal Testosterone Preparation in Monkey (Example 18)

20 mg of test preparation 22 shown in Table 1 was delivered into the right nasal cavity of conscious male cynomolgus monkeys (body weight 5.73 to 5.64 kg; n=2; SNBL, Ltd.), which has a nasal cavity structure similar to that of a human, with a respiratory region delivery device having an air generating part having a maximum air pressure of 28 kPa, a maximum air pressure reaching time of 88 msec, and a constant air pressure continuous delivery time (≥5 kPa) of 146 msec. For measurement of the blood testosterone concentration, blood was collected from the femoral vein with a syringe containing heparin Na before administration and 10, 30, 60, and 240 minutes after administration (5 times in total). The testosterone concentration was measured by chemiluminescent enzyme immunoassay involving Abbott Architect i2000 (ARCHITECT Testosterone, Abbott Japan). This test was performed after being approved by the Animal Experimentation Ethics Committee of SNBL, Ltd.

Figure 6:
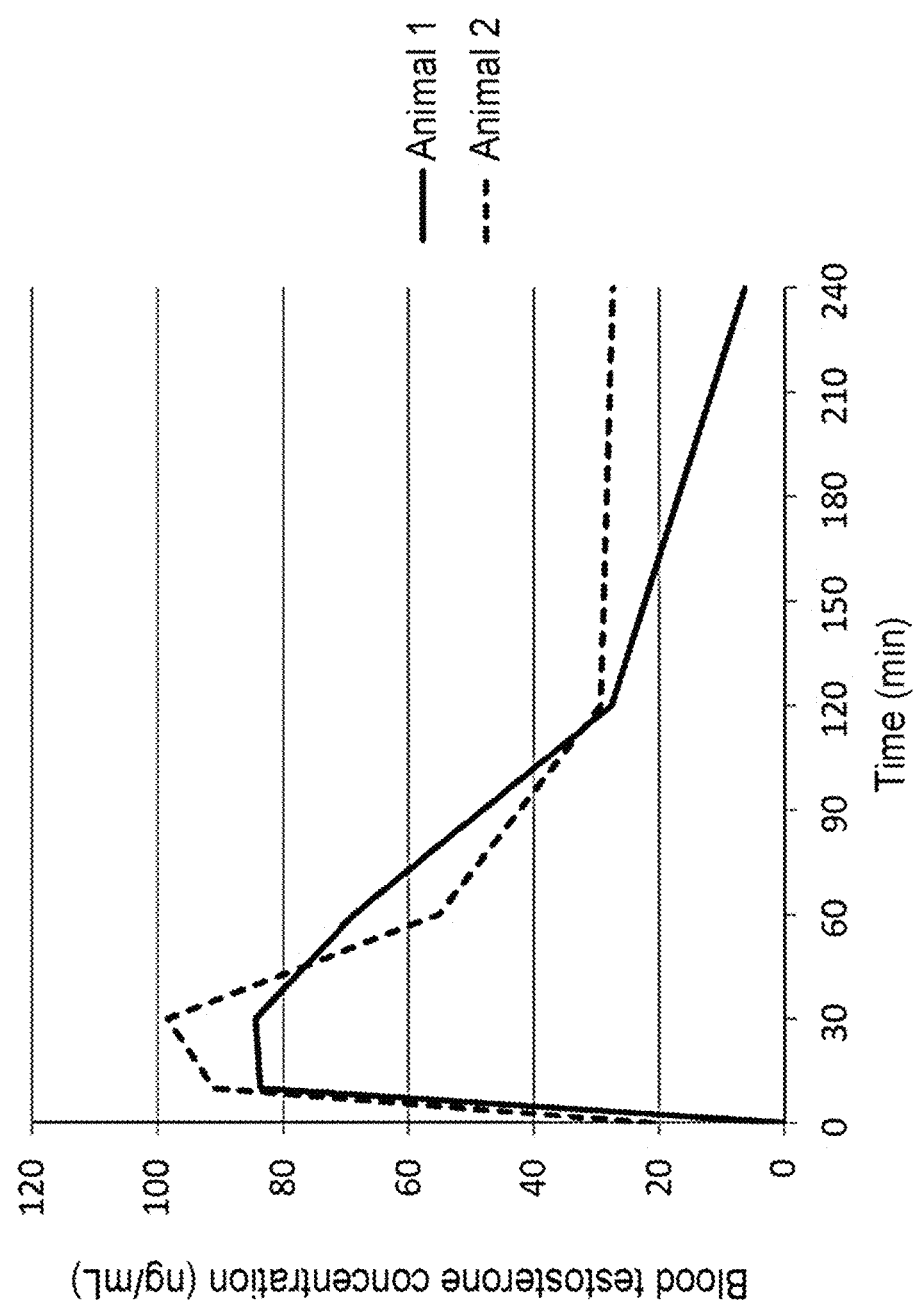
FIG. 6 shows blood testosterone concentrations after selectively administering a testosterone preparation to the respiratory region in the nasal cavity.

Table 7 and FIG. 6 show transition of the blood testosterone concentration. As is clear from Table 7 and FIG. 6, a remarkable increase of the blood testosterone concentration was observed from 10 minutes after administration, and the maximum blood concentration ($C_{max}$) was reached 30 minutes after administration. Accordingly, it was verified that the respiratory region delivery system according to the present invention increases the nasal mucosal absorbability of the active ingredient.

TABLE 7

Blood testosterone concentrations after intranasal administration of the testosterone preparation in monkey

| | | Time (min) | | | | | | PK parameter | | |
|---|---|---|---|---|---|---|---|---|---|---|
| | | Testosterone concentration (ng/mL) | | | | | | | | |
| | Animal No. | Before administration | 10 | 30 | 60 | 120 | 240 | $T_{max}$ (min) | $C_{max}$ (ng/mL) | $AUC_{0-t}$ (ng*min/mL) |
| Example 18 | 1 | 0.0 | 83.7 | 84.4 | 68.7 | 27.6 | 6.3 | 30 | 84.4 | 8485.5 |
| | 2 | 21.0 | 91.1 | 98.4 | 55.1 | 29.3 | 27.4 | 30 | 98.4 | 10027.5 |

7. Evaluation of Absorbability for Nasal Testosterone Preparation in Monkey (Comparative Example 12)

20 mg of test preparation 28 shown in Table 1 was delivered into the right nasal cavity of conscious male cynomolgus monkeys (body weight 4.94 to 5.76 kg; n=6; SNBL, Ltd.), which have a nasal cavity structure similar to that of a human, with a respiratory region delivery device having an air generating part having a maximum air pressure of 28 kPa, a maximum air pressure reaching time of 88 msec, and a constant air pressure continuous delivery time ($\geq 5$ kPa) of 146 msec. For measurement of the blood testosterone concentration, blood was collected from the femoral vein with a syringe containing heparin Na before administration and 5, 10, 20, 30, 45, 60, 120, and 240 minutes after administration (9 times in total). The testosterone concentration was measured by electrochemiluminescence immunoassay involving Cobas 8000 (ECLusys TESTO II, Roche Diagnostics KK).

Figure 7:
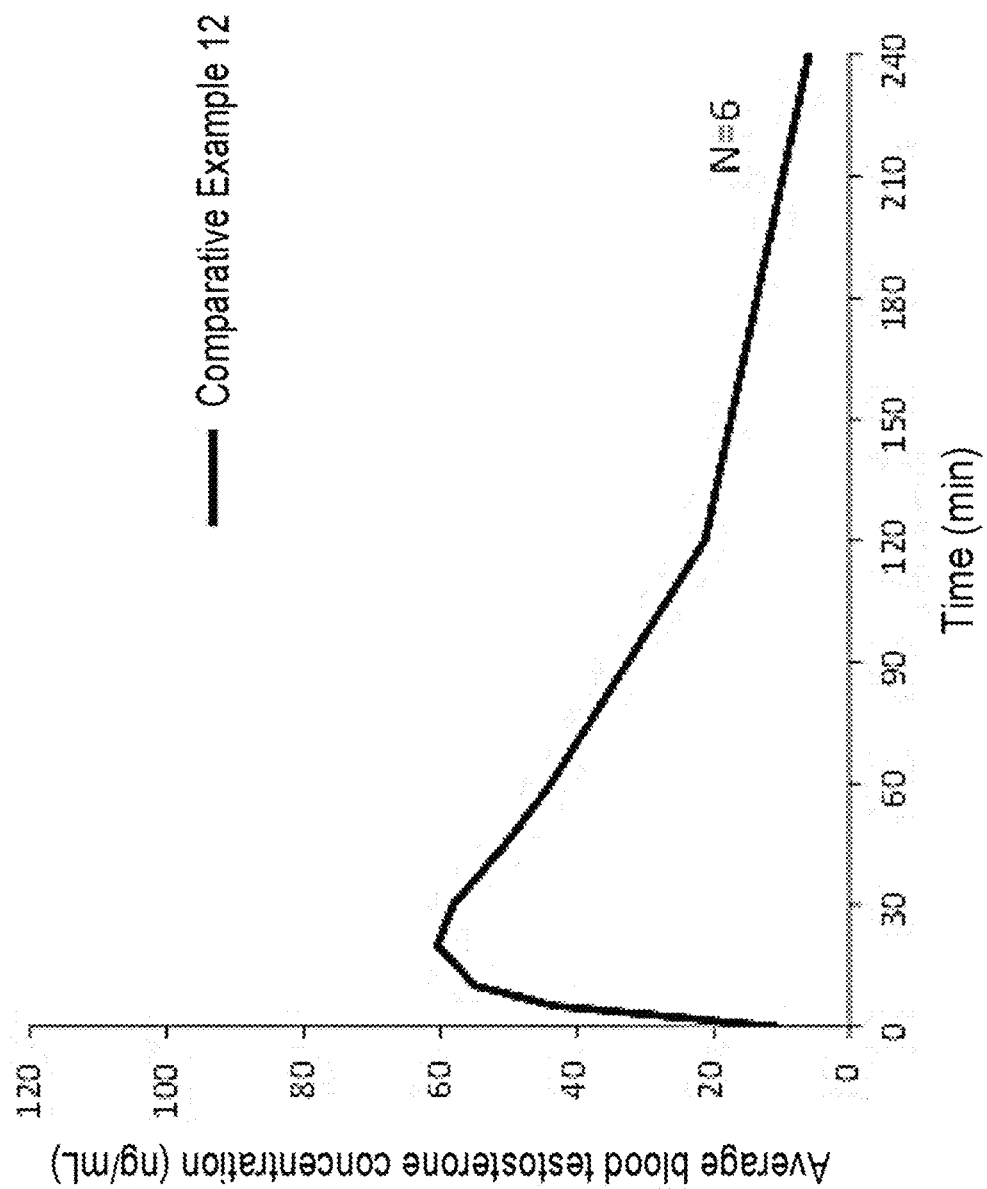
FIG. 7 shows blood testosterone concentrations after administering a testosterone preparation intranasally.

Table 8 and FIG. 7 show transition of the blood testosterone concentration of Comparative Example 12. As is clear from the comparison of Table 7 and FIG. 6 relating to the respiratory region delivery system according to the present invention, it was verified that in Comparative Example 12 in which the test preparation is not effectively distributed in the respiratory region, the nasal mucosal absorbability of the active ingredient was lower than that in Example 18.

TABLE 8

Blood testosterone concentrations after intranasal administration of the testosterone preparation in monkey

| | Animal No. | Before administration | Time (min)/Blood testosterone concentration (ng/mL) | | | | | | | | PK parameter | | |
|---|---|---|---|---|---|---|---|---|---|---|---|---|---|
| | | | 5 | 10 | 20 | 30 | 45 | 60 | 120 | 240 | $T_{max}$ (min) | $C_{max}$ (ng/mL) | $AUC_{0-t}$ (ng*min/mL) |
| Comparative | 1 | 5.5 | 34.7 | 42.2 | 45.2 | 45.0 | 37.1 | 31.2 | 9.2 | 2.6 | 20 | 45.2 | 4228.8 |
| Example 12 | 2 | 12.0 | 39.4 | 46.9 | 59.1 | 52.9 | 52.5 | 48.1 | 20.0 | 6.3 | 20 | 59.1 | 6600.3 |
| | 3 | 25.6 | 55.9 | 70.0 | 71.9 | 63.0 | 50.6 | 40.8 | 22.7 | 2.9 | 20 | 71.9 | 6881.0 |
| | 4 | 1.8 | 45.2 | 57.4 | 61.2 | 69.9 | 59.4 | 50.7 | 29.2 | 11.6 | 30 | 69.9 | 8263.0 |
| | 5 | 11.9 | 41.4 | 49.8 | 57.6 | 56.2 | 49.0 | 44.0 | 28.7 | 8.6 | 20 | 57.6 | 7372.8 |
| | 6 | 9.2 | 42.1 | 62.7 | 67.3 | 61.6 | 53.9 | 47.7 | 17.7 | 4.1 | 20 | 67.3 | 6583.0 |
| Average | | 11.0 | 43.1 | 54.8 | 60.4 | 58.1 | 50.4 | 43.8 | 21.3 | 6.0 | 22 | 61.8 | 6654.8 |
| Standard deviation | | 8.2 | 7.2 | 10.5 | 9.2 | 8.7 | 7.4 | 7.1 | 7.5 | 3.6 | 4 | 10.0 | 1345.1 |

8. Evaluation of Brain Migration for Nasal Oxytocin Preparation in Monkey (Example 19)

25 mg of test preparation 27 shown in Table 1 was delivered into the right nasal cavity of conscious male cynomolgus monkeys (body weight 3.94 to 5.77 kg; n=6; SNBL, Ltd.), which have a nasal cavity structure similar to that of a human, with an olfactory region delivery device having an air generating part having a maximum air pressure of 59 kPa, a maximum air pressure reaching time of 0 msec, and a constant air pressure continuous delivery time ($\geq 10$ kPa) of 69 msec.

As Comparative Example 13, a solution of oxytocin (0.4 mg/mL) dissolved in physiological saline was intravenously delivered into the forearm of conscious male cynomolgus monkeys (body weight 3.91 to 5.29 kg; n=6; SNBL, Ltd.), which have a nasal cavity structure similar to that of a human.

In order to measure the blood oxytocin concentration, blood was collected from the femoral vein with a syringe (dispensed into an EDTA-2K-containing blood collection tube) before administration and 2, 5, 10, 30, 60, 120, 240 and 480 minutes after administration (9 times in total). In order to measure the cerebrospinal fluid oxytocin concentration, cerebrospinal fluid was collected via a catheter indwelled in the cisterna magna before administration and 10, 30, 60, 120, 240 and 480 minutes after administration (7 times in total). The oxytocin concentration was measured by an EIA method involving an Oxytocin Enzyme Immunoassay Kit: Extraction-Free (Peninsula Laboratories International). This test was performed after being approved by the Animal Experimentation Ethics Committee of SNBL, Ltd.

Figure 8:
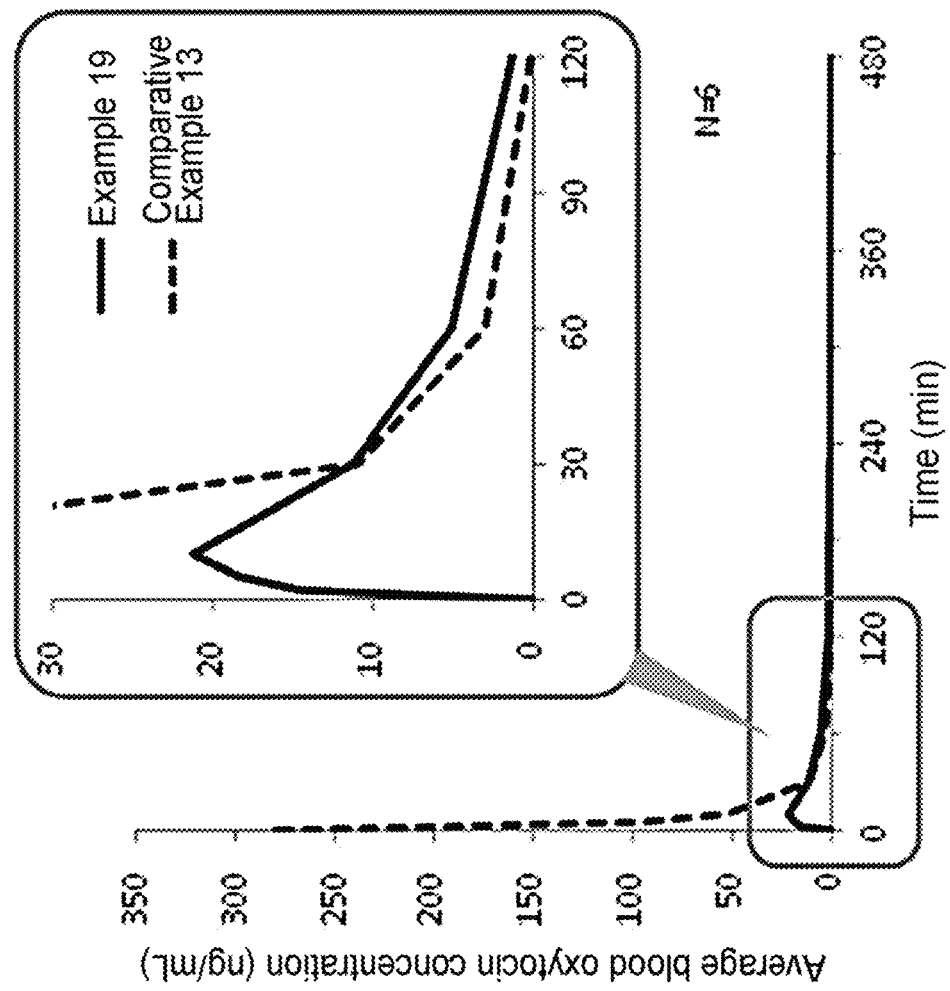
FIG. 8 shows blood oxytocin concentrations after selectively administering oxytocin preparations to the olfactory region in the nasal cavity and administering intravenously, respectively.
Figure 9:
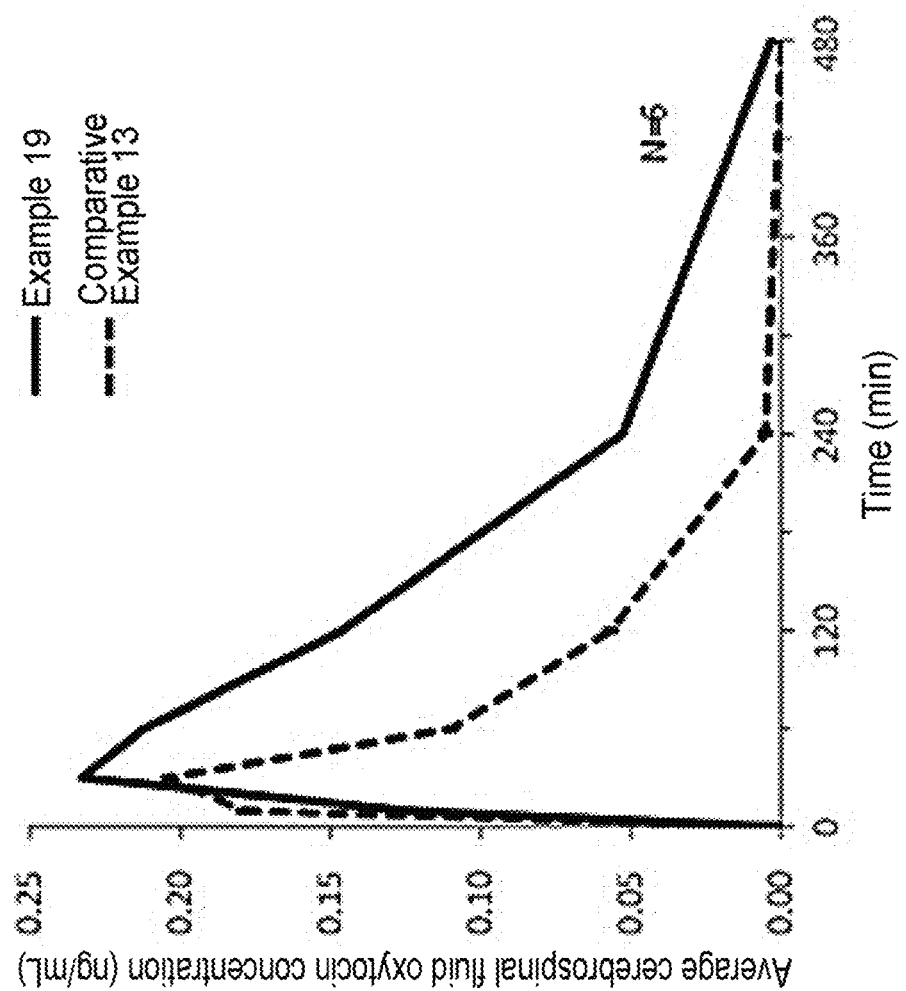
FIG. 9 shows oxytocin concentrations in cerebrospinal fluid after selectively administering oxytocin preparations to the olfactory region selected in the nasal cavity and administering intravenously, respectively.

As is clear from the blood oxytocin concentrations shown in Table 9 and FIG. 8, the blood concentration of Example 19 showed a remarkably lower value than Comparative Example 13. On the other hand, as for the oxytocin concentrations in cerebrospinal fluid shown in Table 10 and FIG. 9, it was found that Example 19 showed a higher value than Comparative Example 13 unlike the results of comparing blood concentrations.

TABLE 9

Blood oxytocin concentrations in monkey

| | Animal No. | Time (min)/Blood oxytocin concentration (ng/mL) | | | | | | | | PK parameter | | |
|---|---|---|---|---|---|---|---|---|---|---|---|---|
| | | 2 | 5 | 10 | 30 | 60 | 120 | 240 | 480 | $T_{max}$ (min) | $C_{max}$ (ng/mL) | $AUC_{0-t}$ (ng*min/mL) |
| Example 19 | 1 | 7.40 | 9.85 | 10.30 | 5.50 | 2.75 | 1.00 | 0.00 | 0.00 | 10 | 10.30 | 537.9 |
| | 2 | 16.65 | 17.05 | 13.60 | 10.75 | 5.65 | 2.00 | 1.00 | 0.00 | 5 | 17.05 | 1162.8 |
| | 3 | 9.20 | 12.20 | 18.10 | 11.50 | 6.80 | 2.10 | 1.05 | 0.00 | 10 | 18.10 | 1269.6 |
| | 4 | 16.30 | 22.80 | 24.15 | 13.20 | 5.35 | 1.25 | 0.00 | 0.00 | 10 | 24.15 | 1117.1 |
| | 5 | 13.40 | 19.25 | 25.05 | 10.95 | 4.10 | 0.55 | 0.00 | 0.00 | 10 | 25.05 | 931.4 |
| | 6 | 23.85 | 29.30 | 36.20 | 15.60 | 6.00 | 1.10 | 0.00 | 0.00 | 10 | 36.20 | 1388.3 |
| Average | | 14.46 | 18.41 | 21.23 | 11.25 | 5.11 | 1.33 | 0.34 | 0.00 | 9.2 | 21.81 | 1067.8 |
| Standard deviation | | 5.91 | 7.10 | 9.32 | 3.35 | 1.46 | 0.60 | 0.53 | 0.00 | 2.0 | 8.85 | 301.4 |
| Comparative Example 13 | 1 | 222.00 | 110.00 | 48.40 | 10.50 | 2.80 | 0.00 | 0.00 | 0.00 | — | 222.00 | 2285.2 |
| | 2 | 246.00 | 101.00 | 64.20 | 15.00 | 4.50 | 1.10 | 0.00 | 0.00 | — | 246.00 | 2840.7 |
| | 3 | 205.00 | 116.00 | 55.10 | 11.80 | 2.90 | 0.00 | 0.00 | 0.00 | — | 205.00 | 2355.1 |
| | 4 | 168.00 | 68.00 | 40.40 | 7.10 | 2.50 | 0.00 | 0.00 | 0.00 | — | 168.00 | 1721.7 |
| | 5 | 202.00 | 68.40 | 50.00 | 9.60 | 2.80 | 0.00 | 0.00 | 0.00 | — | 202.00 | 2060.7 |
| | 6 | 190.00 | 105.00 | 55.70 | 11.60 | 2.60 | 0.00 | 0.00 | 0.00 | — | 190.00 | 2244.9 |
| Average | | 205.50 | 94.73 | 52.30 | 10.93 | 3.02 | 0.18 | 0.00 | 0.00 | — | 205.50 | 2251.4 |
| Standard deviation | | 26.73 | 21.16 | 8.04 | 2.62 | 0.74 | 0.45 | 0.00 | 0.00 | — | 26.73 | 367.7 |

TABLE 10

Cerebrospinal fluid oxytocin concentrations in monkey

| | Animal No. | Time (min) Cerebrospinal fluid oxytocin concentration (ng/mL) | | | | | | | PK parameter | | |
|---|---|---|---|---|---|---|---|---|---|---|---|
| | | Before administration | 10 | 30 | 60 | 120 | 240 | 480 | $T_{max}$ (min) | $C_{max}$ (ng/mL) | $AUC_{0-t}$ (ng*min/mL) |
| Example 19 | 1 | 0.000 | 0.000 | 0.000 | 0.026 | 0.000 | 0.000 | 0.000 | 60 | 0.026 | 1.2 |
| | 2 | 0.000 | 0.042 | 0.140 | 0.258 | 0.224 | 0.078 | 0.000 | 60 | 0.258 | 49.9 |
| | 3 | 0.000 | 0.062 | 0.248 | 0.262 | 0.298 | 0.176 | 0.020 | 120 | 0.298 | 79.8 |
| | 4 | 0.000 | 0.000 | 0.138 | 0.124 | 0.054 | 0.000 | 0.000 | 30 | 0.138 | 13.9 |
| | 5 | 0.000 | 0.382 | 0.488 | 0.344 | 0.168 | 0.046 | 0.000 | 30 | 0.488 | 56.8 |
| | 6 | 0.000 | 0.266 | 0.384 | 0.260 | 0.134 | 0.018 | 0.000 | 30 | 0.384 | 40.6 |
| Average | | 0.000 | 0.125 | 0.233 | 0.212 | 0.146 | 0.053 | 0.003 | 55.0 | 0.265 | 40.4 |
| Standard deviation | | 0.000 | 0.160 | 0.179 | 0.115 | 0.109 | 0.067 | 0.008 | 35.1 | 0.166 | 28.8 |
| Comparative Example 13 | 1 | 0.000 | 0.221 | 0.241 | 0.068 | 0.062 | 0.000 | 0.000 | 30 | 0.241 | 18.0 |
| | 2 | 0.000 | 0.235 | 0.276 | 0.128 | 0.070 | 0.000 | 0.000 | 30 | 0.276 | 22.5 |
| | 3 | 0.000 | 0.253 | 0.292 | 0.183 | 0.093 | 0.032 | 0.000 | 30 | 0.292 | 33.5 |
| | 4 | 0.000 | 0.149 | 0.173 | 0.091 | 0.033 | 0.000 | 0.000 | 30 | 0.173 | 13.6 |
| | 5 | 0.000 | 0.127 | 0.121 | 0.095 | 0.012 | 0.000 | 0.000 | 10 | 0.127 | 10.3 |
| | 6 | 0.000 | 0.091 | 0.122 | 0.095 | 0.072 | 0.000 | 0.000 | 30 | 0.122 | 15.2 |
| Average | | 0.000 | 0.179 | 0.204 | 0.110 | 0.057 | 0.005 | 0.000 | 26.7 | 0.205 | 18.9 |
| Standard deviation | | 0.000 | 0.066 | 0.076 | 0.041 | 0.029 | 0.013 | 0.000 | 8.2 | 0.075 | 8.3 |

As for Example 19, in order to estimate the extent of migration of the intranasally administered drug to the brain without passing through the blood-brain barrier, DTE % (Drug Targeting Efficiency) and DTP % (Direct Transport Percentage) were calculated based on the following expression (1) and expression (2), respectively, reported by Md, S. et al. (Eur. J. Pharm. Sci., 2013 Feb. 14; 48(3): 393-405). DTE % is an index indicating brain migration in Example 19 relative to the amount of the drug migrated from the blood vessels to the brain being 100%, and DTP % is an index indicating the ratio of the amount of the drug migrated from those other than the blood vessels to the brain relative to the total amount of the drug migrated to the brain, i.e., the ratio of the drug directly migrated from the nose to the brain without involving blood.

$$\text{DTE \%} = [AUC_{0-t(in,\ csf)}/AUC_{0-t(in,\ plasma)}]/[AUC_{0-t(iv,\ csf)}/AUC_{0-t(iv,\ plasma)}] \times 100 \quad \text{(Expression 1)}$$

$$\text{DTP \%} = [AUC_{0-t(in,\ csf)} - F]/AUC_{0-t(in,\ csf)} \times 100 \quad \text{(Expression 2)}$$

$$F = AUC_{0-t(iv,\ csf)} \times AUC_{0-t(in,\ plasma)}/AUC_{0-t(iv,\ plasma)}$$

In expressions (1) and (2), $AUC_{0-t(in,\ csf)}$: Area under cerebrospinal fluid oxytocin concentration-time curve of Example 19

$AUC_{0-t\ (in,\ plasma)}$: Area under blood oxytocin concentration-time curve of Example 19

$AUC_{0-t(iv,\ csf)}$: Area under cerebrospinal fluid oxytocin concentration-time curve of Comparative Example 13

$AUC_{0-t(iv,\ plasma)}$: Area under blood oxytocin concentration-time curve of Comparative Example 13

DTE % and DTP % of Example 19 were 450.7% and 77.8%, respectively, and it was found that in Example 19, the drug efficiently migrated from the nose to the brain without involving blood.

The invention claimed is:

1. A method comprising administering a powder preparation to an olfactory region in a nasal cavity, wherein the powder preparation comprises an active ingredient, the powder preparation having a bulk density of 0.1 to 0.5 g/cm$^3$, and a Hausner ratio of 1.6 to 2.4;

wherein the powder preparation is injected into the nasal cavity at a maximum air pressure of 15 to 80 kPa;

wherein the maximum air pressure is reached at 0 to 30 msec;

wherein the powder preparation is continuously injected at an air pressure of 10 kPa or more for a duration of 20 to 80 msec; and wherein 20% by weight or more of the active ingredient delivered into the nasal cavity is distributed in the olfactory region.

2. A method for treating a central nervous system disease, or for performing an examination or diagnosis or a pre-operational or pre-examination treatment based on action on a central nervous system, comprising administering a powder preparation to an olfactory region in a nasal cavity of a patient in need thereof, wherein the powder preparation comprises an active ingredient, the powder preparation having a bulk density of 0.1 to 0.5 g/cm$^3$, and a Hausner ratio of 1.6 to 2.4;

wherein the powder preparation is injected into the nasal cavity at a maximum air pressure of 15 to 80 kPa;

wherein the maximum air pressure is reached at 0 to 30 msec;

wherein the powder preparation is continuously injected at an air pressure of 10 kPa or more for a duration of 20 to 80 msec; and wherein 20% by weight or more of the active ingredient delivered into the nasal cavity is distributed in the olfactory region.

3. A method comprising administering a powder preparation to a respiratory region in a nasal cavity, wherein the powder preparation comprises an active ingredient, the powder preparation having a bulk density of 0.2 to 1.1 g/cm$^3$, and a Hausner ratio of 1.0 to 2.2;

wherein the powder preparation is injected into the nasal cavity at a maximum air pressure of 5 to 40 kPa;

wherein the maximum air pressure is reached at 53 to 150 msec;

wherein the powder preparation is continuously injected at an air pressure of 5 kPa or more for a duration of 40 to 200 msec;

wherein 50% by weight or more of the active ingredient delivered into the nasal cavity is distributed in the respiratory region; and wherein 0% to 5% by weight of the active ingredient delivered into the nasal cavity is distributed in an olfactory region.

4. A method for treating a systemic disease, or for performing an examination or diagnosis or a pre-operational or pre-examination treatment, comprising administering a powder preparation to a respiratory region in a nasal cavity of a patient in need thereof, wherein the powder preparation comprises an active ingredient, the powder preparation having a bulk density of 0.2 to 1.1 g/cm$^3$, and a Hausner ratio of 1.0 to 2.2;

wherein the powder preparation is injected into the nasal cavity at a maximum air pressure of 5 to 40 kPa;

wherein the maximum air pressure is reached at 53 to 150 msec;

wherein the powder preparation is continuously injected at an air pressure of 5 kPa or more for a duration of 40 to 200 msec;

wherein 50% by weight or more of the active ingredient delivered into the nasal cavity is distributed in the respiratory region; and wherein 0% to 5% by weight of the active ingredient delivered into the nasal cavity is distributed in an olfactory region.

5. A method for treating an infection, comprising administering a powder preparation to a respiratory region in a nasal cavity of a patient in need thereof, wherein the powder preparation comprises an active ingredient, the powder preparation having a bulk density of 0.2 to 1.1 g/cm$^3$, and a Hausner ratio of 1.0 to 2.2;

wherein the powder preparation is injected at a maximum air pressure of 5 to 40 kPa;

wherein the maximum air pressure is reached at 53 to 150 msec;

wherein the powder preparation is continuously injected at an air pressure of 5 kPa or more for a duration of 40 to 200 msec;

wherein the infection is at least one of bacterial infection, fungal infection or viral infection;

wherein 50% by weight or more of the active ingredient delivered into the nasal cavity is distributed in the respiratory region; and wherein 0% to 5% by weight of the active ingredient delivered into the nasal cavity is distributed in an olfactory region.

6. The method according to claim 1, wherein the powder preparation has a specific surface area of 0.3 to 2.5 m$^2$/g.

7. The method according to claim 2, wherein the powder preparation has a specific surface area of 0.3 to 2.5 m$^2$/g.

8. The method according to claim 1, wherein the powder preparation has an average particle diameter of 10 to 150 μm.

9. The method according to claim 2, wherein the powder preparation has an average particle diameter of 10 to 150 μm.

10. The method according to claim 3, wherein the powder preparation has a specific surface area of 0.2 to 2.5 m$^2$/g.

11. The method according to claim 4, wherein the powder preparation has a specific surface area of 0.2 to 2.5 m$^2$/g.

12. The method according to claim 5, wherein the powder preparation has a specific surface area of 0.2 to 2.5 m$^2$/g.

13. The method according to claim 3, wherein the powder preparation has an average particle diameter of 10 to 500 μm.

14. The method according to claim 4, wherein the powder preparation has an average particle diameter of 10 to 500 μm.

15. The method according to claim 5, wherein the powder preparation has an average particle diameter of 10 to 500 μm.

16. A method for preventing an infection, comprising administering a powder preparation to a respiratory region in a nasal cavity of a patient in need thereof, wherein the powder preparation comprises an active ingredient, the powder preparation having a bulk density of 0.2 to 1.1 g/cm$^3$, and a Hausner ratio of 1.0 to 2.2;

wherein the powder preparation is injected at a maximum air pressure of 5 to 40 kPa;

wherein the maximum air pressure is reached at 53 to 150 msec;

wherein the powder preparation is continuously injected at an air pressure of 5 kPa or more for a duration of 40 to 200 msec;
wherein the infection is at least one of bacterial infection, fungal infection or viral infection;
wherein the active ingredient is a vaccine;
wherein 50% by weight or more of the active ingredient delivered into the nasal cavity is distributed in the respiratory region; and
wherein 0% to 5% by weight of the active ingredient delivered into the nasal cavity is distributed in an olfactory region.

\* \* \* \* \*